(12) United States Patent
Wall et al.

(10) Patent No.: US 9,187,726 B2
(45) Date of Patent: Nov. 17, 2015

(54) CULTURING A MICROORGANISM IN A MEDIUM WITH AN ELEVATED LEVEL OF A CARBOXYLATE COUNTERION SOURCE

(75) Inventors: Thomas E. Wall, Austin, TX (US); You Chen, San Diego, CA (US); Stanley Bower, San Diego, CA (US); Wendy Loza, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 82 days.

(21) Appl. No.: 13/324,636

(22) Filed: Dec. 13, 2011

(65) Prior Publication Data

US 2012/0184002 A1   Jul. 19, 2012

Related U.S. Application Data

(60) Provisional application No. 61/426,602, filed on Dec. 23, 2010, provisional application No. 61/426,555, filed on Dec. 23, 2010, provisional application No. 61/426,568, filed on Dec. 23, 2010, provisional application No. 61/426,624, filed on Dec. 23, 2010.

(51) Int. Cl.
| | |
|---|---|
| *A01N 1/02* | (2006.01) |
| *C12N 1/12* | (2006.01) |
| *C12N 1/38* | (2006.01) |
| *C12P 7/64* | (2006.01) |

(52) U.S. Cl.
CPC .. *C12N 1/12* (2013.01); *C12N 1/38* (2013.01); *C12P 7/6409* (2013.01)

(58) Field of Classification Search
USPC ........................................ 435/243
See application file for complete search history.

(56) References Cited

U.S. PATENT DOCUMENTS

| | | | | |
|---|---|---|---|---|
| 5,455,167 A | 10/1995 | Voelker et al. | ............. | 435/172.3 |
| 5,654,495 A | 8/1997 | Voelker et al. | ................. | 800/250 |
| 6,746,857 B2 | 6/2004 | Higashiyama et al. | ....... | 435/134 |
| 2001/0016342 A1* | 8/2001 | Higashiyama et al. | ....... | 435/134 |
| 2004/0214758 A1 | 10/2004 | Meyers et al. | ................. | 514/12 |
| 2009/0298143 A1* | 12/2009 | Roessler et al. | ............. | 435/134 |

FOREIGN PATENT DOCUMENTS

| | | | | |
|---|---|---|---|---|
| WO | WO 2008/151149 | 12/2008 | ............... | C12N 1/00 |
| WO | WO 2010/075483 | 7/2010 | ............... | C12N 9/16 |

OTHER PUBLICATIONS

Malovikova et al. Comparative interactions of magnesium and calcium counterions with polygalacturonic acid. Biopolymers. 1994;34:1059-1064.*
Mishra et al. Calcium and magnesium effect on divalent cation deficient *Hydrilla verticillata* thylakoid electron transport activity. J. Biosci. 1998;23(3):201-207.*
Thibault et al. Interactions of counterions with pectins studied by potentiometry and circular dichroism. American Chemical Society. 1986;6:61-72.*
UTEX. Media detail. The culture collection of algae at the University of Texas at Austin. 2009.*
Reed et al. Osmotic adjustment and organic solute accumulation in unicellular cyanobacteria from freshwater and marine habitats. Marine Biology. 1985;88:1-9.*
Rippka et al. Generic assignments, strain histories and properties of pure cultures of cyanobacteria. Journal of General Microbiology. 1979;111:1-61.*
Adibekian, A., et al. (2012) "Click-generated triazole ureas as ultrapotent, in vivo-active serine hydrolast inhibitors", *Nat Chem Bio*, 7(7): 469-478.
Bateman, A., et al. (2000), "The pfam protein families database", *Nucleic Acids Research*, 28(1):263-266.
Bateman, A., et al. (2004), "The pfam protein families database", *Nucleic Acids Research*, 32: Database Issue: D138-D141.
Finn, R., et al. (2006), "Pfam: clans, web tools and services", *Nucleic Acids Research*, 34: Database Issue 34:D247-D251.
Finn, R., et al. (2010), "The pham protein families database", *Nucleic Acids Research*, 38: Database Issue 38:D211-D222.
Heger, A., et al. (2003), "Exhaustive enumeration of protein domain families", *J. Mol. Biol*. 328; 749-767.
International Search Report for PCT/US11/64652 dated Apr. 5, 2012.
Petschow, B., et al. (1996), "Susceptibility of *Helicobacter pylori* to bactericidal properties of medium-chain monoglycerides and free fatty acids", *Antimicrobial Agents and Chemotherapy*, 40(2): 302-306.
Sonnhammer, E., et al. (1998), "Pfam: multiple sequence alignments and HMM-profiles of protein domains" *Nucleic Acids Research* 26(1):320-322.
Wu, C., et al. (2009), "Identification of novel esterase from metagenomic library of yangtze river", *J. Microbiol. Biotechnol*, 19(2): 187-193.

* cited by examiner

*Primary Examiner* — Robert Mondesi
*Assistant Examiner* — Lynn Y Fan
(74) *Attorney, Agent, or Firm* — Harness, Dickey & Pierce, P.L.C.

(57) ABSTRACT

The invention provides a method of culturing a microorganism that produces a free fatty acid in a culture medium, comprising culturing the microorganism in the culture medium comprising a sufficient amount (e.g., at least about 0.5 mM) of a carboxylate counterion source to enhance viability of the microorganism in the culture medium. Fatty acids produced using the methods of the invention can be used to synthesize a variety of products, including biofuels.

18 Claims, 4 Drawing Sheets

CULTURING A MICROORGANISM IN A MEDIUM WITH AN ELEVATED LEVEL OF A CARBOXYLATE COUNTERION SOURCE

CROSS-REFERENCE TO RELATED APPLICATIONS

This application claims benefit of priority to (i) U.S. provisional patent application 61/426,602 filed Dec. 23, 2010 of the same title, (ii) U.S. provisional patent application 61/426,555 filed Dec. 23, 2010 entitled "Prokaryotic Acyl-ACP Thioesterases for Producing Fatty Acids in Genetically Engineered Microorganisms", (iii) U.S. provisional patent application 61/426,568 filed Dec. 23, 2010 entitled "Genetically Engineered Microorganisms Comprising 4-Hydroxybenzoyl-CoA Thioesterases and Methods of Using the Same for Producing Fatty Acids and Fatty Acid Derivatives" and (iv) U.S. provisional patent application 61/426,624 filed Dec. 23, 2010 entitled "Lipase-Mediated Production of Free Fatty Acids by Recombinant Microorganisms", each of which is hereby incorporated by reference in its entirety.

REFERENCE TO A SEQUENCE LISTING

This application contains references to amino acid sequences and/or nucleic acid sequences which have been submitted concurrently herewith as the sequence listing text file entitled "2010EM385 (PM0014)_ST25.txt", file size 42.6 KiloBytes (KB), created on Dec. 12, 2011. The aforementioned sequence listing is hereby incorporated by reference in its entirety pursuant to 37 C.F.R. §1.52(e)(5).

TECHNICAL FIELD

The present invention relates, in some embodiments, to methods of culturing microorganisms for the production of lipid molecules, such as fatty acids.

BACKGROUND

Fossil fuel is a general term for buried combustible geologic deposits of organic materials, formed from decayed plants and animals that have been converted to crude oil, coal, natural gas, or heavy oils by exposure to heat and pressure in the earth's crust over hundreds of millions of years. The utilization of fossil fuels has enabled large-scale industrial development and largely supplanted water driven mills, as well as the combustion of wood or peat for heat. Fossil fuels are a finite, non-renewable resource. The burning of fossil fuels by humans is a source of emissions of carbon dioxide. In addition, other air pollutants, such as nitrogen oxides, sulfur dioxide, volatile organic compounds (VOCs) and heavy metals are produced. The concentrations of several greenhouse gases, such as carbon dioxide, have increased over time. According to the global warming hypothesis, an increase in greenhouse gas emissions from industry and agriculture has played a role in global warming.

Increased demand for energy by the global economy has also placed increasing pressure on the cost of hydrocarbons. Aside from energy, many industries, including plastics and chemical manufacturers, rely heavily on the availability of hydrocarbons as a feedstock for their manufacturing processes. Cost-effective alternatives to current sources of supply could help mitigate the upward pressure on energy and these raw material costs.

One approach for the cost-effective alternatives utilizes free fatty acid production by microorganisms. Culturing the microorganisms, however, is difficult as a high level of free fatty acid in a culture environment is toxic to many microorganisms. For example, a culture of fatty-acid producing microorganisms may accumulate a toxic level of free fatty acids over a period of hours or days. In addition, the toxicity of the free fatty acid in the culture environment may cause a selective pressure to reduce the expression levels of genes associated with free fatty acid production by the microorganisms.

SUMMARY OF THE INVENTION

The invention provides a method of culturing a microorganism that produces a free fatty acid comprising culturing the microorganism in a culture medium comprising at least about 0.5 mM (e.g., at least about 1 mM, at least about 2 mM, at least about 2.5 mM, at least about 3 mM, at least about 4 mM, at least about 5 mM, at least about 8 mM, at least about 10 mM, at least 20 mM, or at least about 25 mM) of a carboxylate counterion source (e.g., a soap-forming counterion source, such as an alkaline earth metal ion source or a transition metal ion source). Optionally but preferably, the microorganism releases at least one free fatty acid into the culture medium. The soap-forming counterion source can comprise a multivalent counterion source, such as but not limited to a divalent counterion source. For example, the counterion source can comprise magnesium, calcium, strontium, chromium, manganese, iron, cobalt, nickel, copper, zinc, aluminum, or a combination thereof. Additionally or alternately, the medium used in the culturing methods can contain a counterion such as magnesium and/or calcium in at least two-fold the amount present in a standard culture medium, such as a standard medium for culturing microalgae or cyanobacteria. In some embodiments, the medium can contain at least about 0.5 mM (e.g., at least about 1 mM, at least about 2 mM, at least about 2.5 mM, at least about 3 mM, at least about 4 mM, at least about 5 mM, at least about 8 mM, at least about 10 mM, at least 20 mM, or at least about 25 mM) magnesium and/or calcium. Independently or in combination with other embodiments, the microorganism can exhibit greater viability or a higher growth rate in the medium comprising at least about 0.5 mM of a carboxylate counterion source, such as an alkaline earth metal ion source or a transition metal ion source, than in a medium that comprises about 0.25 mM or less of an alkaline earth metal or transition metal ion source.

Additionally but preferably, the microorganism can be viable in a culture medium that has an elevated level of a soap-forming carboxylate counterion source, such as at least 0.5 mM of a soap-forming counterion source, and/or can comprise at least about 200 mg/L (e.g., at least about 400 mg/L or at least about 800 mg/L) of free fatty acids. Free fatty acids present in the culture medium can be of a single chain length (e.g., an acyl chain length of 6, 8, 10, 12, 14, 16, 18, 20, 22, or 24 carbons) or can be a mixture of fatty acids having two or more of these different acyl chain lengths.

The invention includes methods of producing one or more free fatty acids using a culture medium that includes at least 0.5 mM of a carboxylate counterion source, such as a transition metal ion source or an alkaline earth metal ion source, as disclosed herein. The microorganism cultured in the medium can produce at least one free fatty acid (e.g., at least one $C_6$-$C_{24}$ fatty acid). The microorganism can preferably produce one or more free fatty acids, where at least 10% (e.g., at least 20%, at least 30%, at least 40%, at least 50%, at least 60%, at least 70%, at least 80%, or at least 90%) of the population of free fatty acids produced by the microorganism can comprise or be a $C_6$, $C_8$, $C_{10}$, $C_{12}$, $C_{14}$, $C_{16}$, $C_{18}$, $C_{20}$, $C_{22}$, or $C_{24}$ free fatty acid, or a mixture of two or more fatty acids having any of these different acyl chain lengths.

The microorganism used in any of the methods disclosed herein can comprise an exogenous or recombinant nucleic acid molecule encoding a thioesterase and/or a lipase. In some embodiments, the microorganism can include an exogenous gene encoding a thioesterase such as an acyl-ACP thioesterase, an acyl-CoA thioesterase, a hydroxylbenzoyl-CoA thioesterase, or a combination thereof. Additionally or alternatively, the microorganism can include a recombinant nucleic acid molecule encoding a polypeptide having lipolytic activity, such as, for example, a lipase, for example a lipase that is a member of the Pfam AB Hydrolase clan CL0028, such as a gene encoding an amino acid sequence that is included in Pfam PF01674, Pfam F01764, Pfam PF07819, Pfam PF03583, or Pfam PF00151.

In some embodiments, the recombinant microorganism can be a photosynthetic microorganism, such as a microalga or a cyanobacterium. Microalgae can include for example, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* and *Volvox* species, including freshwater and marine microalgal species of these or other genera. *Cyanobacterium* can include, for example, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus* species, including freshwater and marine cyanobacterial species of these or other genera.

In some embodiments, the medium used for culturing a fatty acid-producing microorganism can be a standard culture medium that includes at least 0.5 mM (e.g., at least 1 mM, at least 2 mM, at least 2.5 mM, at least 3 mM, at least 4 mM, at least 5 mM, at least 8 mM, at least 10 mM, at least 20 mM, or at least 25 mM) of magnesium, calcium, strontium, chromium, manganese, iron, cobalt, nickel, copper, zinc, or aluminum. In some embodiments, the medium used for culturing of a fatty acid-producing microorganism can be a counterion-supplemented standard culture medium having substantially the same composition as a standard culture medium with the exception that a greater amount of a carboxylate counterion (e.g., magnesium, calcium, strontium, chromium, manganese, iron, cobalt, nickel, copper, aluminum, and/or zinc ion) is present in the counterion-supplemented culture medium with respect to the standard culture medium. In further embodiments, at least one alkaline earth metal salt, such as but not limited to calcium acetate, calcium borate, calcium carbonate, calcium chloride, calcium citrate, calcium gluconate, calcium hydroxide, calcium lactate, calcium maleate, calcium nitrate, calcium orotate, calcium phosphate, calcium salicylate, calcium sulfate, magnesium acetate, magnesium borate, magnesium carbonate, magnesium chloride, magnesium gluconate, magnesium hydroxide, magnesium lactate, magnesium maleate, magnesium nitrate, magnesium orotate, magnesium phosphate, magnesium salicylate, and/or magnesium sulfate can be added to a culture medium, such as but not limited to a standard culture medium to provide a concentration of at least 0.5 mM (e.g., at least 1 mM, at least 2 mM, at least 2.5 mM, at least 3 mM, at least 4 mM, at least 5 mM, at least 8 mM, at least 10 mM, at least 20 mM, or at least 25 mM) of an alkaline earth metal such as calcium and/or magnesium in the culture medium.

The invention provides methods of producing one or more free fatty acids that include culturing a microorganism that can produce one or more free fatty acids and can optionally but preferably release at least one of the free fatty acids into a culture medium that comprises at least about 0.5 mM of a carboxylate counterion source such as a a soap-forming counterion source where the counterion can be a metal (e.g., an alkaline earth metal or a transition metal). Independently or in combination with other embodiments, the microorganism can exhibit greater viability in the medium that comprises at least about 0.5 mM of a carboxylate counterion, such as an alkaline earth metal or a transition metal, than in a medium that comprises about 0.25 mM or less of a carboxylate counterion, such as an alkaline earth metal or transition metal in the culture medium. The counterion source can comprise a multivalent counterion source, such as but not limited to a divalent counterion source. Additionally or alternately, the counterion source can comprise, for example, magnesium, calcium, strontium, chromium, manganese, iron, cobalt, nickel, copper, zinc, aluminum, or a combination thereof. Still further additionally or alternately, the medium can contain magnesium and/or calcium in an at least 2-fold the amount present in a standard algal culture medium. For example, the medium can contain at least about 1 mM (e.g., at least about 2 mM, at least about 2.5 mM, at least about 3 mM, at least about 4 mM, at least about 5 mM, at least about 8 mM, at least about 10 mM, at least about 20 mM, or at least about 25 mM) of magnesium and/or calcium.

Methods for producing one or more free fatty acids, in some embodiments, can additionally include isolating one or more free fatty acids from the culture. In such embodiments, the microorganism can be cultured for a period of at least one day (e.g., at least three days, at least five days, at least seven days, at least ten days, at least fifteen days, at least twenty days, at least twenty-five days, or at least thirty days) prior to isolating/removing free fatty acids from the culture. The microorganism, which in certain embodiments can be a photosynthetic organism, such as, but not limited to, a cyanobacterial strain, can be grown to an optical density as measured at about 730 nm of at least 6.0 (e.g., at least 8.0, at least 10.0, or at least 12.0) prior to isolating/removing free fatty acids from the culture medium. One or more free fatty acids can be isolated from the culture medium, the microorganism, or both using any feasible methods. Additionally or alternately, one or more free fatty acids can be isolated from the culture medium by recovering solid or semi-solid free fatty acids complexed with one or more (metal) counterions (e.g., as a soap). Capture of (semi-)solid fatty acids and/or fatty acid salts can be accomplished, for example, by any one or combination of skimming, scooping, pumping, filtering, the use of adsorbing particles/substrates, or the like.

Also provided herein is a culture of a microorganism that produces at least one free fatty acid, in which the culture medium can include at least one carboxylate counterion source, such as an alkaline metal ion source or a transition metal ion source, at a concentration of at least 0.5 mM, at least 1 mM, at least 2 mM, at least about 2.5 mM, at least 3 mM, at least 4 mM, at least 5 mM, at least 8 mM, at least 10 mM, at least 20 mM, or at least 25 mM in which the microorganism can release the at least one free fatty acid into the culture medium. The carboxylate counterion source can be, for example, a soap-forming counterion source, such as, for example, an alkaline earth metal ion source or a transition metal ion source. In further examples, the carboxylate counterion source present in the culture medium can be at least one alkaline earth metal salt, such as a calcium salt or a magnesium salt, such as but not limited to calcium acetate, calcium borate, calcium carbonate, calcium chloride, calcium citrate, calcium gluconate, calcium hydroxide, calcium lactate, calcium maleate, calcium nitrate, calcium orotate, calcium phosphate, calcium salicylate, calcium sulfate, magnesium acetate, magnesium borate, magnesium carbonate, magnesium chloride, magnesium gluconate, magnesium hydroxide, magnesium lactate, magnesium maleate, magnesium nitrate, magnesium orotate, magnesium phosphate, magnesium salicylate, and/or magnesium sulfate.

Additionally, the amount of free fatty acid produced by the microorganism and present in the culture medium can be at least 100 μg/mL (e.g., at least 200 μg/mL, at least 400 μg/mL, at least 600 μg/mL, at least 800 μg/mL, or at least 1 mg/mL). At least one of the accumulated free fatty acids present in the culture medium can have an acyl chain length of between 6 and 24 carbons (e.g, a C8, C10, C12, C14, C16, or C18 chain length). In some embodiments, at least 20% (e.g., at least 30%, at least 40%, at least 50%, at least 60%, at least 70%, or at least 80%) of the free fatty acid(s) present in the culture medium can be C8 free fatty acid(s), C10 free fatty acid(s), C12 free fatty acid(s), C14 free fatty acid(s), C16 free fatty acid(s), or some combination thereof. The free fatty acid(s) present in the culture medium can optionally be complexed or associated with the carboxylate counterion provided in the culture medium and can be soluble or in solid or semi-solid form, for example, the free fatty acids may be present in the culture medium as a gel, film, colloid, fine particulate, particulate aggregate, or the like, or some combination thereof, that may be dispersed or suspended in the culture medium or floating at the surface of the culture medium.

The fatty acid-producing microorganism can be any microorganism, for example, the microorganism of the cell culture can be a eubacterium, archaebacterium, fungus, yeast, heterokont, cyanobacterium, or alga. According to some embodiments of the present invention, the host microorganism is a photosynthetic microorganism, such as various photosynthetic bacteria, including a cyanobacterium, or alga, including a eukaryotic microalgal species. The fatty acid producing microorganism can be a recombinant microorganism that includes an exogenous or non-native nucleic acid molecule encoding at least one thioesterase, such as, for example, an acyl-ACP thioesterase, an acyl-CoA thioesterase, or a hydroxylbenzoyl thioesterase, and/or at least one exogenous or non-native polypeptide having lipolytic activity, for example a lipase, such as but not limited to a lipase that is a member of the Pfam AB Hydrolase clan, CL0028, such as, but not limited to, a lipase that is a member of Pfam 01674, Pfam 01764, Pfam 07819, Pfam 03583, and/or Pfam 00151. A recombinant microorganism of a fatty acid-producing cell culture can include one or more exogenous or non-native genes encoding, for example, one or more of any combination of a thioesterase, a lipase, a polypeptide regulating fatty acid biosynthesis, and a polypeptide that participates in fatty acid biosynthesis. For example, a recombinant microorganism producing free fatty acids can include two or more exogenous or non-native genes, where the two or more exogenous or non-native genes can be present on the same or different nucleic acid molecules. The fatty acids produced by the recombinant microorganism can used for the production of chemicals or fuels, and optionally be converted to any of various derivatives, including hydrocarbons, esters, or alcohols.

BRIEF DESCRIPTION OF THE DRAWINGS

FIG. 2 provides data on the growth of genetically modified cyanobacterial strains producing free fatty acids in calcium-supplemented media.

DETAILED DESCRIPTION

Figure 1:
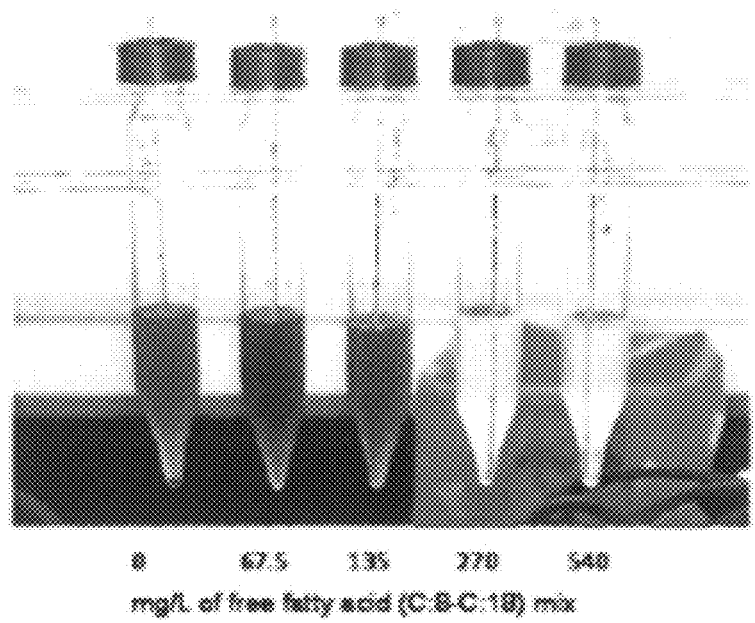
FIG. 1 depicts cultures of *Synechocystis* PCC 6803 grown for six days in the presence of a free fatty acid mixture. The tubes (left to right) contained 0 μg/mL, ~67.5 μg/mL, ~135 μg/mL, ~270 μg/mL, and ~540 μg/mL of a free fatty acid mixture that included $C_8$, $C_{10}$, $C_{12}$, $C_{14}$, $C_{16}$, and $C_{18}$ free fatty acids. The tubes that include 0 μg/mL, ~67.5 μg/mL, and ~135 μg/mL of the free fatty acid mixture show the culture medium is dark, indicating dense growth of the cultures, whereas the tubes that include ~270 μg/mL, and ~540 μg/mL of a free fatty acid mixture show have colorless growth media, indicating lack of cell growth.

As described herein, the present invention in various embodiments provides a method of culturing a microorganism that can produce a free fatty acid in a culture medium comprising at least about 0.5 mM of a carboxylate counterion source, such as an alkaline earth metal ion source or a transition metal ion source. In one aspect, the microorganism can exhibit greater viability, a higher growth rate, or both, in the medium comprising at least about 0.5 mM of an alkaline earth metal ion source or a transition metal ion source than in a medium that comprises about 0.25 mM of an alkaline earth metal ion source or a transition metal ion source. Optionally but preferably, the microorganism can release at least one free fatty acid into the culture medium.

Releasing and secreting, as used herein, can interchangeably refer to active and/or passive transport mechanisms, wherein fatty acids are able to cross the cell membrane. Examples of such transport mechanisms can include, but are not necessarily limited to, gradient diffusion, facilitated diffusion, active transport, and combinations thereof. The microorganism used in the methods and cultures disclosed herein can produce at least one free fatty acids having an acyl chain length from six to twenty-four carbons, for example, from eight to eighteen carbons. Additionally or alternatively, the microorganism as disclosed herein that produces at least one free fatty acid can produce one, two, three, four, or more free fatty acids, in which at least one of the free fatty acids produced can be a $C_8$ fatty acid and/or a $C_{10}$ fatty acid. Further additionally or alternately, the microorganism as disclosed herein that produces at least one free fatty acid can produce one, two, three, four, or more free fatty acids, in which at least one of the free fatty acids produced can be a $C_{12}$ fatty acid, a $C_{14}$ fatty acid, and/or a $C_{16}$ fatty acid. Still further additionally or alternatively, at least 20 wt %, for example at least 30 wt %, at least 40 wt %, at least 50 wt %, at least 60 wt %, at least 70 wt %, at least 80 wt %, or at least 90 wt %, of the at least one free fatty acid produced, and optionally released into the growth medium, by the microorganism can be a $C_8$ fatty acid, and/or at least 20 wt %, for example at least 30 wt %, at least 40 wt %, at least 50 wt %, at least 60 wt %, at least 70 wt %, at least 80 wt %, or at least 90 wt %, of the at least one free fatty acid produced, and optionally released into the growth medium, by the microorganism can be a $C_{10}$ fatty acid. In yet further additional or alternative embodiments, at least 20 wt %, for example at least 30 wt %, at least 40 wt %, at least 50 wt %, at least 60 wt %, at least 70 wt %, at least 80 wt %, or at least 90 wt %, of the at least one free fatty acid produced and/or released into the growth medium, by the microorganism can be a $C_{12}$ fatty acid, and/or at least 20 wt %, for example at least 30 wt %, at least 40 wt %, at least 50 wt %, at least 60 wt %, at least 70 wt %, at least 80 wt %, or at least 90 wt %, of the at least one free fatty acid produced, and optionally released into the growth medium, by the microorganism can be a $C_{14}$ fatty acid. Yet still further additionally or alternately, at least 20 wt %, for example at least 30 wt %, at least 40 wt %, at least 50 wt %, at least 60 wt %, at least 70 wt %, at least 80 wt %, or at least 90 wt %, of the at least one free fatty acid produced, and optionally released into the growth medium, by the microorganism can be a $C_{16}$ fatty acid, and/or at least 20 wt %, for example at least 30 wt %, at least 40 wt %, at least 50 wt %, at least 60 wt %, at least 70 wt %, at least 80 wt %, or at least 90 wt %, of the at least one free fatty acid produced, and optionally released into the growth medium, by the microorganism can be a $C_{18}$ fatty acid.

Without limiting the invention to any particular mechanism, it is noted that certain carboxylate counterions are able to complex with some fatty acids, resulting in the fatty acids precipitating out of the solution as "soap", a term used herein to denote a metallic salt of a fatty acid. In the context of the methods and cultures disclosed herein, "resulting in the fatty acids precipitating out of solution" is meant that the counterion-fatty acid complex (or soap) can be in the form of a solid or semi-solid, for example, the counterion-fatty acid complex can be present as a gel, semi-solid, "scum", film, colloid, fine particulate, particulate, solid, aggregate, or the like, or combination thereof, that may be dispersed, suspended, entrained, or the like, within the culture medium, that may, for example, settle to the bottom of the culture vessel, float on top of the aqueous culture medium, adhere to the walls or other parts of the culture vessel, adhere to particles or structures within the culture, or a combination thereof. Examples of metals that can complex with fatty acids and/or ionically bond with fatty acid carboxylate ions are referred to herein as "soap forming" metals (or soap forming counterions), and can include, but are not limited to, magnesium, calcium, strontium, barium, beryllium, lead, iron, nickel, cobalt, tin, chromium, aluminum, zinc, copper, and combinations thereof. Some metals, such as, for example, the alkaline earth metals calcium and/or magnesium are believed to be compatible with cell growth, and in some embodiments may be particularly suited to the methods of the invention, as addition of calcium and/or magnesium compounds may have little or no detrimental effects on the growth of cells even at relatively high (millimolar) concentrations. Without limiting the scope or practice of the invention to any particular mechanism, it is possible that, by forming soaps with fatty acids in the culture medium, the counterion complexation/ionic bonding with the free fatty acids can eliminate or dramatically reduce the ability of the free fatty acids to exert toxic effects on cells, such as but not limited to any surfactant effects.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. Nonlimiting examples of selected and/or controlled conditions can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism can be grown heterotrophically or mixotrophically, using both light and a reduced carbon source. Additionally or alternately, the microorganism can be cultured phototrophically. When growing phototrophically, the microorganism can advantageously use light as an energy source. In certain embodiments, the growth media of the culture do not include a reduced carbon source, or at least a substantial amount of a reduced carbon source. As used herein, a "substantial amount of a reduced carbon source" is an amount that can support growth of the culture in the absence of another energy source. An inorganic carbon source, such as $CO_2$ or bicarbonate, can be used for synthesis of biomolecules by the microorganism. "Inorganic carbon," as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. If an organic carbon molecule or compound is provided in the culture medium of a microorganism grown phototrophically, it generally cannot be taken up and/or metabolized by the cell for energy and/or typically is not present in an amount sufficient to provide sustainable energy for the growth of the cell culture.

Solid and liquid growth media are generally available from a wide variety of sources, as are instructions for the preparation of particular media suitable for a wide variety of strains of microorganisms. For example, various fresh water and salt water media can include those described in Barsanti, L. and Gualtieri, P. (2005) Algae: Anatomy, Biochemistry, and Biotechnology, CRC Press, Taylor & Francis Group, Boca Raton, Fla., USA, which is incorporated herein by reference for media and methods for culturing algae, or in the examples of PCT Publication No. WO 2008/151149, which is herein incorporated by reference. Algal media recipes can also be found at the websites of various algal culture collections, including, as nonlimiting examples, the UTEX Culture Collection of Algae (sbs.utexas.edu/utex/media.aspx); Culture Collection of Algae and Protozoa (ccap.ac.uk/media/pdfrecipes.htm); and Katedra Botaniky (/botany.natur.cuni.cz/algo/caup-media.html).

In some embodiments, media used for culturing an organism that produces fatty acids can include at least about 0.5 mM of a carboxylate counterion source, such as a soap-forming counterion source. "Soap-forming counterion source" refers to any source of an ion that interacts with at least a portion of the fatty acid(s) to form monovalent or multivalent salts and/or to form soap precipitates (which can be in the form of a gel, sol, "scum", film, or the like, that can be suspended/dispersed/entrained in, and/or floats in or on, the culture medium, and/or that can associate with the walls of and/or other structures within the culture vessel). For example, fatty acids complexed with counterion sources, including, but not limited to, calcium and/or magnesium, may form fatty acid calcium salts and/or fatty acid magnesium salts (calcium and/or magnesium "soaps").

In some embodiments, a culture medium used in the methods that includes at least about 0.5 mM of an alkaline earth metal can be a medium that can include sea water (for example, at least about 5 wt % sea water) and/or artificial sea water. Seawater and artificial seawater media can typically include calcium at a concentration, for example, from about 0.5 mM to about 15 mM, and therefore are examples of media useful in the methods provided herein for culturing a microorganism that can produce at least one free fatty acid in a culture medium having at least one soap-forming counterion source, such as an alkaline earth metal ion source, at a concentration of 0.5 mM or greater. In alternate embodiments, the medium can be a supplemented medium, whether characterized as a fresh water medium or a salt water medium, for culturing microalgae and/or cyanobacteria, that can include an elevated level of a transition metal and/or an alkaline earth metal, such as, for example, magnesium and/or calcium, with respect to a known or published recipe for the media (where a published recipe is a recipe provided in a published book or article, or available on an internet site, as a medium for culturing a microorganism). "Fresh water media", including fresh water media supplemented with a carboxylate counterion source, e.g., fresh water media supplemented with calcium and/or magnesium, can be used for culturing of fresh water and/or salt water microorganisms, as many microorganisms isolated from salt water environments or classified as marine microorganisms do not necessarily require salt water growth media and/or do not necessarily exhibit significant growth deficits in fresh water media.

Addition of a carboxylate counterion source to the medium can improve the viability of a microorganism in media that includes a relatively high concentration (e.g., greater than 100 mg/L, greater than 200 mg/L, greater than 300 mg/L, greater than 400 mg/L, or greater than 500 mg/L) of free fatty acid(s). Additionally or alternatively, fatty acid-producing strains can advantageously be more robust with excess carboxylate counterion source content. A soap-forming counterion source, for example, includes an inorganic counterion source, an alkaline earth metal ion source, a transition metal ion source, a multivalent (i.e., having a valence of +2 or higher) counterion source, a divalent counterion source, or some combination.

In embodiments where carboxylate counterion sources are present in the culture medium, their concentration may be greater than or equal to the concentration of free fatty acids in the culture medium, in which case, most, if not all, of the free fatty acids may be in a form where the carboxylate version of the free fatty acid(s) is(are) ionically associated with the carboxylate counterion. Additionally or alternately, in embodiments where carboxylate counterion sources are present in the culture medium, their concentration may be less than the concentration of free fatty acids in the culture medium, in which case, a portion of the free fatty acids may be in a form where the carboxylate version of the free fatty acid(s) is(are) ionically associated with the carboxylate counterion (herein abbreviated as "soap form" for convenience only), and another portion of the free fatty acids may be in a form where the carboxylate version of the free fatty acid(s) is(are) not ionically associated with the carboxylate counterion (herein abbreviated as "toxic form" for convenience only). Further additionally or alternately, the concentration of the multivalent counterion source in the culture medium can be sufficient to yield no more than about 150 mg/L of the toxic form (and/or not the soap form) of the free fatty acid(s) in the culture medium, for example no more than about 125 mg/L, no more than about 100 mg/L, no more than about 80 mg/L, no more than about 65 mg/L, no more than about 50 mg/L, no more than about 40 mg/L, no more than about 30 mg/L, no more than about 20 mg/L, or no more than about 10 mg/L.

In some embodiments, the culture medium can comprise an increased concentration of a carboxylate counterion source, for example a soap-forming counterion source, such as a metal (typically provided as a salt and/or in an ionic form), with respect to a standard medium formulation, such as, for example, standard BG-11 medium (ATCC Medium 616, Table 2), or a modified medium such as ATCC Medium 854 (BG-11 modified to contain vitamin B12) or ATCC Medium 617 (BG-11 modified for marine cyanobacteria, containing additional NaCl and vitamin B12). The counterion source can include, but is not limited to, magnesium, calcium, iron, strontium, barium, beryllium, lead, nickel, cobalt, tin, chromium, aluminum, zinc, copper, or the like, or combinations thereof (particularly multivalent metals, such as magnesium, calcium, and/or iron).

Accordingly, in some embodiments, the present invention can include a calcium-supplemented standard culture medium having the same composition as a standard culture medium with the exception that a greater amount of calcium is present than in the standard culture medium. Additionally or alternately, at least one calcium salt can be added to the standard culture medium, where the at least one calcium salt can comprise or be any of calcium acetate, calcium carbonate, calcium chloride, calcium citrate, calcium gluconate, calcium hydroxide, calcium lactate, calcium nitrate, calcium phosphate, calcium sulfate, or other calcium salts, or a combination thereof. Additional or alternate embodiments can include a magnesium-supplemented standard culture medium having the same composition as a standard culture medium with the exception that a greater amount of magnesium is present than in the standard culture medium. Additionally or alternatively, at least one magnesium salt can be added to the standard culture medium, where the at least one magnesium salt can comprise or be any of magnesium acetate, magnesium carbonate, magnesium chloride, magnesium citrate, magnesium gluconate, magnesium hydroxide, magnesium lactate, magnesium nitrate, magnesium phosphate, magnesium sulfate, other magnesium salts, or a combination thereof.

For example, a medium used for growing microorganisms that produce free fatty acids can include at least 2-fold, for example at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold the amount of a carboxylate counterion source as compared to a standard medium, such as, for example, a standard algal growth medium. Additionally or alternatively, the medium used for growing microorganisms can include, for example, at least about 0.5 mM, between about 0.5 mM and about 1 mM, between about 1 mM and about 2 mM, between about 2 mM and about 5 mM, between about 5 mM and about 10 mM, between about 10 mM and about 25 mM, or greater than 25 mM of a carboxylate counterion source in the formulation. Further additionally or alternatively, the medium used for growing microorganisms can include, for example, at least about 1 mM, for example at least about 2 mM, at least about 2.5 mM, at least about 3 mM, at least about 4 mM, at least about 5 mM, at least about 8 mM, at least about 10 mM, at least about 20 mM, at least about 25 mM, or at least about 50 mM of a carboxylate counterion source in the formulation.

According to some embodiment of the present invention, the culture medium may contain no free fatty acid at the beginning of the culturing period, with the microorganism producing and optionally also releasing and/or secreting at least one free fatty acid later in the culture process, such that the culture medium at a time point after free fatty acid production is initiated includes accumulated free fatty acids, for example, a culture medium can include at least about 100 mg/L, at least about 200 mg/, at least about 400 mg/L, at least about 600 mg/L, at least about 800 mg/L, or at least about 1000 mg/L accumulated free fatty acids. The free fatty acids present in the culture medium can be associated with a carboxylate counterion, or additionally or alternatively, the culture medium may further contain relatively insoluble fatty acids and/or free fatty acids that do not substantially interact with a carboxylate counterion.

Other conventional biologically active ingredients can be added to the culture by known means. For example, the culture methods can include inducing expression of a thioesterase gene, a lipase gene, and/or other gene for the production of free fatty acids. Inducing expression can include adding a nutrient or compound to the culture, removing one or more components from the culture medium, increasing or decreasing light and/or temperature, and/or other manipulations that promote expression of the lipase, thioesterase, and/or other gene. Such manipulations can largely depend on the nature of the promoter operably linked to the thioesterase, lipase, or other gene.

"Viability" of a microorganism can be determined by measuring the number of days before visible bleaching of the culture, and/or without a decline in cell count or optical density (for example, depending on the species of microorganism, at a wavelength of between 550 and 750 nm, such as at an $OD_{600}$ or an $OD_{730}$) with respect to a control microorganism, for example, the same microorganism cultured in a medium that does not include a particular counterion source or in a standard culture medium that includes only a standard level of a particular counterion source. Viability can additionally or alternatively be assessed by assaying cells at the end of a given time period during which fatty acids are being produced and/or are present in a culture. For example, a microorganism would have a greater viability in medium A than in medium B if, after a set time period in culture, there is less visible bleaching of the microorganism medium A culture than in the medium B culture, and/or if there is no decline in OD and/or cell count in the medium A culture with respect to the medium B (or a control) culture. In another example, a microorganism would have a greater viability in a first medium than in a second medium if, after a given time period, there were a higher density of cells in the first culture, as assessed by cell counts, OD measurement, or other tests. Other tests for viability as they are known in the art can additionally or alternatively be used, for example, assays that rely on the presence of dyes that indicate lack of integrity of the cell membrane and/or assays that can indicate the metabolic status of the cell. For instance, assays can use the fluorogenic esterase substrates (e.g., calcein AM, BCECF AM, various fluorescein diacetate derivatives, and/or the like), nucleic acid stains (e.g., aminoactidimycin D, SYTO stains, SYTOX stains, ethidium or propidium dyes, and/or the like), assays that measure oxidation or reduction (for example, using indicators such as resazurin, dodecylresazurin, dihydrorhodamines or dihydrofluoresceins, 3,4,5,6-pentafluorotetramethyldihydrorosamine, tetrazolium salts, 3-(4,5-dimethylthiazol-2-yl)-2,5-phenyltetrazolium bromide (MTT), and/or the like). In various embodiments, a dye/stain/detection reagent can be selected such that the absorption and/or emission spectra do not significantly overlap that of the pigments of the cells (for example, chlorophylls and/or phycobilins) In some cases, it may be desirable to quantitate the proportion of living to dead cells using microscopy, plate assay, flow cytometry, or the like. Reagents and kits for measuring cell viability are commercially available, for example, from Life Technologies Inc. (Carlsbad, Calif.).

In some embodiments, the microorganism cultured in a medium as described above can be viable in a culture medium that comprises at least about 200 mg/L free fatty acids and/or free fatty acid derivatives, for example at least about 400 mg/L, at least about 600 mg/L, at least about 800 mg/L, or at least about 1000 mg/L.

Microorganisms

The microorganism that produces at least one free fatty acid can be any microorganism, including without limitation, a eubacterium, archaebacterium, fungus, yeast, heterokont, cyanobacterium, alga, or the like. According to some embodiments of the present invention, the host microorganism is a photosynthetic microorganism. Photosynthetic microorganisms useful as host organisms can include, but are not limited to, any photosynthetic microorganisms capable of converting inorganic carbon into a substrate that can, in turn, be converted to fatty acids and/or fatty acid derivatives. These photosynthetic microorganisms can include prokaryotes as well as eukaryotic organisms, such as various algae, including microalgae and diatoms.

In some embodiments, microorganisms can include eukaryotic algae and cyanobacteria (blue-green algae). Representative eukaryotic algae can include, but are not limited to, green algae (chlorophytes), red algae (rhodophytes), diatoms (bacillariophytes), prasinophytes, glaucophytes, chlorarachniophytes, euglenophytes, chromophytes, and dinoflagellates. The microorganisms according to some embodiments of the present invention can include, but are not limited to, the following genera of microalgae: *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera,*

*Cricosphaera, Crypthecodinium, Cryptomonas, Cyclotella, Dunahella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* and *Volvox,* including freshwater and marine microalgal species of these or other genera.

The microorganisms according to some embodiments of the present invention can include, but not limited to, the following genera of cyanobacteria: *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus,* including freshwater and marine cyanobacterial species of these or other genera. For example, the recombinant photosynthetic microorganism can be a *Synechococcus, Synechocystis,* or *Thermosynechococcus* species. Alternatively, the recombinant photosynthetic microorganism can be a *Cyanobium, Cyanothece,* or *Cyanobacterium* species, or further alternatively, the recombinant photosynthetic microorganism can be a *Gloeobacter, Lyngbya* or *Leptolyngba* species.

Microorganisms that can be useful in accordance with the methods of the present invention can be found in various locations and environments throughout the world. Without being bound by theory, it is observed that, perhaps as a consequence of their isolation from other species and/or their evolutionary divergence, the particular growth medium for optimal growth and generation of lipid and/or hydrocarbon constituents can vary. In some cases, certain strains of microorganisms may be unable to grow in a particular growth medium because of the presence of some inhibitory component or the absence of some essential nutritional requirement required by the particular strain of microorganism.

A number of cyanobacterial species are known and have been manipulated using molecular biological techniques, including but not limited to the unicellular cyanobacteria *Synechocystis* sp. PCC6803 and *Synechococcus elongates* PCC7942, whose genomes have been completely sequenced.

The recombinant microorganism in some embodiments does not substantially accumulate triacylglycerols (TAGs) during the culturing period. Additionally or alternately, the recombinant microorganism can express an exogenous gene (such as a thioesterase and/or lipase gene) during the period of culturing when lipid synthesis is occurring. In some such particular embodiments, expression of the exogenous gene(s) does not result in production of an alkyl ester, such as a fatty acid ethyl ester, fatty acid propyl ester, fatty acid methyl ester, or the like, and preferably results in production of a free fatty acid.

Genetic Modification

In some embodiments, the microorganism can be a genetically engineered microorganism that includes an exogenous nucleic acid molecule encoding a thioesterase and/or a lipase for production of additional free fatty acids, which can optionally but preferably be released or secreted into the culture medium.

"Exogenous nucleic acid molecule" refers to a nucleic acid molecule that codes for the expression of an RNA and/or protein that has been introduced ("transformed") into a cell (or a progenitor of a cell). A transformed cell may be referred to as a recombinant cell, into which additional exogenous gene(s) may be introduced. The exogenous gene may be from a different species (and so "heterologous"), or from the same species (and so "homologous"), relative to the cell being transformed. An "endogenous" nucleic acid molecule, gene, or protein is the organism's own nucleic acid molecule, gene, or protein as it occurs in, or is naturally produced by, the organism.

When referring to a gene regulatory sequence or to an auxiliary nucleic acid sequence used for maintaining or manipulating a gene sequence (e.g., a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome, or episome. Thus, a promoter operably linked to a gene to which it is not operably linked to in its natural state (i.e., in the genome of a non-genetically engineered organism) is referred to herein as a "heterologous promoter", even though the promoter may be derived from the same species (or, in some cases, the same organism) as the gene to which it is linked.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a host cell, subjected to laboratory manipulation, and reintroduced into a host cell is considered "non-native."

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the term recombinant, engineered, or genetically engineered refers to organisms that have been manipulated by introduction of an exogenous or recombinant nucleic acid sequence into the organism, and includes organisms having gene knockouts, targeted mutations and gene replacement, promoter replacement, deletion, or insertion, as well as organisms having exogenous genes that have been introduced into the organism. An exogenous or recombinant nucleic acid molecule can be integrated into the recombinant/genetically engineered organism's genome or in other instances may not be integrated into the recombinant/genetically engineered organism's genome.

A thioesterase is an enzyme that catalyzes the cleavage of a fatty acid. For example, an "acyl-ACP thioesterase" is an enzyme that catalyzes the cleavage of a fatty acid from an acyl carrier protein (ACP) during lipid synthesis. In some embodiments of the present invention, the exogenous nucleic acid molecule encoding a thioesterase includes, without limitation, an acyl-ACP thioesterase, an acyl-CoA thioesterase, a hydroxylbenzoate-CoA thioesterase, or a combination thereof.

In some embodiments, a microorgansim for the production of free fatty acids can be transformed with a gene encoding an exogenous acyl-ACP thioesterase, such as a gene encoding a polypeptide that, when queried against the Pfam database, provides a match with Pfam PF01643 having a bit score of less than or equal to 20.3 (the gathering cut-off for PF01643), and/or a gene encoding an acyl-ACP thioesterase from a higher plant species. Genes encoding acyl-ACP thioesterases derived from higher plants can include, without limitation, genes encoding acyl-ACP thioesterases from *Cuphea* species (e.g., *Cuphea carthagenesis* (e.g., SEQ ID NO:5), *Cuphea wrightii* (e.g., AAC49784.1 GI:1336008), *Cuphea lanceolata* (e.g., CAA54060, GI495227), *Cuphea palustris*, (e.g., AAC49783.1 GI:1336006; AAC49179.1 GI:1215718); *Cuphea hookeriana* (e.g., AAC72882.1 GI:3859830; AAC49269.1 GI:1292906; AAC72881.1 GI:3859828; AAC72883.1 GI:3859832), *Cuphea calophylla* (e.g., ABB71580.1 GI:81361963), or the like, or combinations thereof) and/or genes from other higher plant species. For example, a microorganism used in the methods and cultures disclosed herein can include a gene encoding an acyl-ACP thioesterase from species such as, but not limited to, *Arabidopsis* (XP_002885681.1 GI:297835598; NP_172327.1 GI:15223236); *Arachis hypogaea* (e.g., ABO38556.1 GI:133754634); *Brassica* species (e.g., CAA52069.1 GI:435011), *Camellia oleifera* (e.g., ACQ57189.1 GI:229358082); *Cinnamonum camphorum* (e.g., AAC49151.1 GI:1143156); *Cocos nucifera; Glycine max* (e.g., ABD91726.1 GI:90192131); *Garcinia mangostana* (e.g., AAB51525.1 GI:1930081); *Gossypium hirsutum* (e.g., AAD01982.1 GI:4104242); *Helianthus annuus* (e.g., AAQ08226 GI:33325244); *Jatropha curcas* (e.g., ABU96744.1 GI:156900676); *Macadamia tetraphylla* (e.g., ADA79524.1 GI:282160399); *Elaeis oleifera* (e.g., AAM09524.1 GI:20067070); *Oryza sativa* (e.g., BAA83582.1 GI:5803272); *Populus tomentosa* (e.g., ABC47311.1 GI:83778888); *Umbellularia califomica* (e.g., AAC49001.1 GI:595955); *Ulmus Americana* (e.g., AAB71731.1 GI:2459533); and *Zea mays* (ACG41291.1 GI:195643646); any of those disclosed in U.S. Pat. Nos. 5,455,167, 5,654,495, and 5,455,167 (all incorporated by reference herein in their entireties); and combinations thereof. Additionally or alternatively, the acyl-ACP thioesterase can be from mosses (*Bryophyta*), such as, for example, *Physcomitrella patens* (e.g., XP_001770108.1 GI:168035219). These examples are not limiting with regard to the types or specific examples of acyl-ACP thioesterase genes that can be used. Additionally or alternately, acyl-ACP thioesterase genes can be from additional organisms, including, for example, prokaryotic organisms. Illustrative examples of prokaryotic acyl-ACP thioesterases that may be expressed by a microorganism useful in the methods and cultures provided herein can include, but are not limited to, acyl-ACP thioesterases from *Parabacteroides distasonis* (e.g., YP_001303423 GI:150008680); *Clostridium thermocellum* (e.g., YP_001039461 GI:125975551); *Desulfovibrio desulfuricans* (e.g., Q312L1 GI:123552742); *Elusimicrobium minutum* (e.g., ACC98705 GI:186971720); *Carboxydothermus hydrogenoformans* (e.g., YP_359670 GI:78042959); *Clostridium thermocellum* (e.g., YP_001039461 GI:125975551); *Moorella thermoacetica* (e.g., YP_431036 GI:83591027); *Geobacter metallireducens* (e.g., YP_384688 GI:78222941); *Salinibacter ruber* (e.g., YP_444210 GI:83814393); *Microscilla marina* (e.g., EAY28464 123988858); *Parabacteroides distasonis* (e.g., YP_001303423 GI:150008680); *Enterococcus faecalis* (e.g., ZP_03949391 GI:227519342); *Lactobacillus plantarum* (e.g., YP_003062170 GI:254555753); *Leuconostoc mesenteroides* (e.g., YP_817783 GI:116617412); *Oenococcus oeni* (e.g., ZP_01544069 GI:118586629); *Mycobacterium smegmatis* (e.g., ABK74560 GI:118173664); *Mycobacterium vanbaalenii* (e.g., ABM11638 GI:119954633); *Rhodococcus erythropolis* (e.g., ZP_04385507 GI:229491686; *Rhodococcus opacus* (e.g., YP_002778825 GI:226361047), variants having at least 80% identity to these or other prokaryotic thioesterases, and combinations thereof.

A gene encoding an acyl-CoA thioesterase can additionally or alternatively be introduced into a host microorganism to generate free fatty acids. An acyl-CoA thioesterase gene transformed into a microorganism for the production of free fatty acids can be from plant, animal, and/or microbial sources. For example, a gene encoding the TesA and/or TesB thioesterase of *E. coli*, and/or a variant thereof, for example, an acyl-CoA thioesterase such as, but not limited to, a variant as disclosed in International Publication No. WO 2010/075483, incorporated by reference herein in its entirety, can be introduced into a microorganism. Additionally or alternately, one or more genes can be transformed into a microorganism that encode proteins that, when queried against the Pfam database of protein families, are identified as members of Pfam PF02551 (acyl-CoA thioesterase), where the bit score is equal to or greater than the gathering cut off (20.7).

Additionally or alternatively, the microorganism can include one or more genes encoding an exogenous 4-hydroxybenzoyl-CoA thioesterase, for example, a gene encoding a polypeptide that recruits to pfam with a bit score of at least 20.6. Among the 4-hydroxybenzoyl-CoA thioesterases considered for use can be, for example, 4-hydroxybenzoyl-CoA thioesterases from *Bacillus* species and *Geobacillus* species, and/or 4-hydroxybenzoyl-CoA thioesterases of *Acidiphilium, Bartonella, Rhodopseudomonas, Magnetospirillum, Burkholderia, Granulibacter, Rhizobium*, and/or *Labrenzia* species, and variants having at least 80% identity to identified or characterized 4-hydroxybenzoyl-CoA thioesterases.

The present invention, in some embodiments, further describes recombinant microorganisms genetically engineered with exogenous and/or endogenous genes encoding polypeptides having lipolytic activity, for example, lipases or thioesterases capable of producing free fatty acids from membrane lipids and/or storage lipids, e.g., phospholipids, triacylglycerols, diacylglycerols, monoacylglycerols, or the like, or combinations thereof. Lipases are enzymes that catalyze the hydrolysis of ester bonds in glycerolipids, including, but not limited to, mono-, di-, and tri-acyl glycerols, as well as combinations thereof, to release free fatty acids and/or alcohols. Ubiquitously present in plants, animals, and microorganisms, lipases have been widely employed in food, chemical, and pharmaceutical industries for various applications.

A lipase gene (or a gene encoding a polypeptide having lipolytic activity) can be a gene encoding any lipase, e.g., that liberates a fatty acid from a glycerolipid (including a monoglyceride, a diglyceride, a triglyceride, a phospholipid, a galactolipid, etc.). For example, a lipase gene can encode a polypeptide having lipase activity that can be a member of the Pfam AB Hydrolase clan, CL0028, such as, but not limited to, a lipase that is a member of Pfam 01674, Pfam 01764, Pfam 07819, Pfam 03583, and/or Pfam 00151. In some embodiments, an exogenous lipase gene introduced into a microorganism can encode a protein with an amino acid sequence having an E-value parameter of 0.01 or less when queried using the Pfam Profile HMM for any of Pfam PF01674, Pfam PF 01764, Pfam PF07819, Pfam PF03583, and/or Pfam PF00151.

"Pfam" is a large collection of protein domains and protein families maintained by the Pfam Consortium and available at several sponsored world wide web sites, including: pfam.sanger.ac.uk/ (Welcome Trust, Sanger Institute); pfam.sbc.su.se/ (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr/. The latest release of Pfam is Pfam 24.0 (October 2009, 11912 families) based on the UniProt protein database release 15.6, a composite of Swiss-Prot release 57.6 and TrEMBL release 40.6. Pfam domains and families are identified using multiple sequence alignments and hidden Markov models (HMMs). Pfam-A families, which are based on high quality assignments, are generated by a curated seed alignment using representative members of a protein family and profile hidden Markov models based on the seed alignment, whereas Pfam-B families are generated automatically from the non-redundant clusters of the latest release of the Automated Domain Decomposition algorithm (ADD; Heger A, Holm L U (2003) J Mol Biol 328(3):749-67). All identified sequences belonging to the family are then used to automatically generate a full alignment for the family (Sonnhammer et al. (1998) Nucleic Acids Research 26: 320-322; Bateman et al. (2000) Nucleic Acids Research 26: 263-266; Bateman et al. (2004) Nucleic Acids Research 32, Database Issue: D138-D141; Finn et al. (2006) Nucleic Acids Research Database Issue 34: D247-251; Finn et al. (2010) Nucleic Acids Research Database Issue 38: D211-222). By accessing the pfam database, for example, using any of the above-reference websites, protein sequences can be queried against the HMMs using HMMER homology search software (e.g., HMMER3, hmmer.janelia.org/). Significant matches that identify a queried protein as being in a pfam family (or as having a particular pfam domain) are those in which the bit score is greater than or equal to the gathering threshold for the Pfam domain. The gathering threshold for the pfam Acyl-ACP thioesterase family (PF01643) is 20.3. Expectation values (e values) can also be used as a criterion for inclusion of a queried protein in a pfam or for determining whether a queried protein has a particular pfam domain, where low e values (much less than 1.0, for example less than 0.1 or less than or equal to 0.01) represent low probabilities that a match is due to chance.

Also considered herein are microorganisms that include nucleic acid molecules encoding variants of the above-listed acyl-ACP thioesterases, acyl-CoA thioesterases, 4-hydroxybenzoyl-CoA thioesterases, and/or lipases, in which the variants have at least 80%, for example at least 85%, at least 90%, at least 95%, at least 97%, at least 98%, or at least 99%, identity to the amino acid sequences accessed by the provided or referenced Genbank Accession Numbers, in which the variants have at least the level of activity (e.g., thioesterase or lipase activity) as the reference sequence.

The term "gene" is used broadly to refer to any segment of nucleic acid (typically DNA, but optionally RNA) associated with expression of a given RNA or protein. Thus, genes include sequences encoding expressed RNA (which can include polypeptide coding sequences) and, often, the regulatory sequences required for their expression. Genes can be obtained from a variety of sources, including cloning from a source of interest or synthesizing from known or predicted sequence information and may include sequences designed to have desired parameters.

In some embodiments, the recombinant microorganisms can be transformed with an isolated nucleic acid molecule encoding one or more polypeptides with a thioesterase and/or lipase activity. Additionally or alternately contemplated are recombinant microorganisms that are engineered to include gene regulatory sequences that induce or increase expression of an endogenous lipase or thioesterase gene. For example, a microorganism can be engineered such that a heterologous promoter is inserted upstream of a coding region of an endogenous lipase gene. The heterologous promoter can replace an endogenous promoter and/or can be inserted upstream or downstream of the endogenous promoter that regulates expression of the endogenous lipase gene, for example using homologous recombination or site-specific recombination. The heterologous promoter can be a constitutive promoter or an inducible promoter that increases expression of the endogenous lipase gene.

In some embodiments, the present invention relates to a recombinant microorganism that includes at least one recombinant expression system for at least one thioesterase gene and/or at least one lipase gene that operates to liberate and/or release fatty acids. A "free fatty acid", as used herein, is meant to refer to a non-esterified acyl moiety that is substantially unassociated, e.g., with an enzyme and/or protein, within or outside an organism (e.g., globular and/or micellular storage within an organism, without esterification, can still qualify as a free fatty acid). Thus, a free fatty acid according to the present invention need not necessarily be a strict acid or be structurally "free", but a free fatty acid specifically does not include an acyl moiety whose carboxylate oxygen is covalently linked to any other moiety other than a hydrogen atom (meaning that fatty acid esters are specifically not included in free fatty acids. However, a free fatty acid can advantageously include an acyl moiety containing at least four carbons (preferably at least 6 carbons, for example at least 8 carbons), in which the acyl moiety (i) is covalently linked to a hydrogen atom, (ii) has an ionic charge, to which a counterion can be associated (even if loosely and/or solvent-separated), and/or (iii) is otherwise associated (not covalently) with another moiety that is relatively easily transformable into the corresponding acid form or the corresponding ionic form (e.g., through hydrogen-bonding or the like). Nonlimiting examples of counterions can include metals salts (such as calcium, magnesium, sodium, potassium, aluminum, iron, and the like, and combinations thereof), other inorganic ions (such as ammonium, mono-, di-, tri-, and tetra-alkylammonium, sulfonium, phosphonium, and the like, and combinations thereof), organic ions (such as carbocations), and the like, and combinations thereof.

Other Modifications

Additionally or alternatively to providing an expression system for one or more appropriate exogenous genes, such as thioesterase and/or lipase genes, further modifications in the microorganism may be made. For example, in addition to having an exogenous thioesterase gene and/or a recombinant lipase gene, a microorganism used in the methods herein may further include at least one additional exogenous nucleic acid molecule that encodes a polypeptide that participates in the synthesis of a fatty acid. For example, a transgenic microorganism for the production of one or more fatty acids can include an exogenous gene encoding an acetyl-CoA carboxylase, a malonyl CoA:ACP transacylase, and/or a beta-ketoacyl-ACP synthase.

In some embodiments, the recombinant microorganism can further include at least one endogenous gene that is attenuated and/or disrupted. Such an endogenous gene that can be attenuated and/or disrupted in the recombinant microorganism can include, but is not limited to, acyl-CoA synthetase, acyl-ACP synthetase, acyl CoA dehydrogenase, glycerol-3-phosphate dehydrogenase, acetaldehyde CoA dehydrogenase, pyruvate dehydrogenase, acetate kinase, and the like, and combinations thereof.

Further additionally or alternatively, the microorganism can be modified such that one or more genes that encode beta-oxidation pathway enzymes have been inactivated and/or downregulated, and/or such that the enzymes themselves that are operative on such beta-oxidation pathways may be inhibited. This could prevent the degradation of fatty acids released from acyl-ACPs, thus enhancing the yield of secreted fatty acids. In cases where the desired products are medium-chain fatty acids, the inactivation and/or downregulation of genes that encode acyl-CoA synthetase and/or acyl-CoA oxidase enzymes that preferentially use these chain lengths as substrates could be beneficial. Mutations in the genes encoding medium-chain-specific acyl-CoA synthetase and/or medium-chain-specific acyl-CoA oxidase enzymes, such that the activity of the enzymes could be diminished, may additionally or alternatively be effective in increasing the yield of produced and/or released fatty acids. An optional additional modification can inactivate and/or downregulate the acyl-ACP synthetase gene and/or can inactivate and/or inhibit the encoded protein. Mutations in the genes can be introduced either by recombinant or non-recombinant methods. These enzymes and their genes are known and may be targeted specifically by disruption, deletion, generation of antisense sequences, generation of ribozymes, and/or other recombinant approaches known to the practitioner. Inactivation of the genes can additionally or alternatively be accomplished by random mutation techniques such as exposure to UV and/or chemical mutagens, and the resulting cells can be screened for successful mutants. The proteins themselves can be inhibited by intracellular generation of appropriate antibodies, intracellular generation of peptide inhibitors, or the like, or some combination thereof.

Still further additionally or alternatively, the microorganism can be modified such that the acyl-ACP synthetase (AAS) gene is inactivated and/or downregulated, or such that the enzymes themselves can be inhibited. Acyl-ACP synthetase (AAS) converts free fatty acid to acyl-ACP for free fatty acid recycling and membrane restructuring, such that mutating AAS strains can advantageously enhance the yield of fatty acids produced by the lipase-expressing microorganisms, e.g., as shown in Example 2.

Again still further additionally or alternatively, the photosynthetic microorganism can be modified such that one or more genes that encode storage carbohydrate and/or polyhydroxyalkanoate (PHA) biosynthesis pathway enzymes can be inactivated and/or downregulated, and/or such that the enzymes themselves that are operative on such pathways can be inhibited. Examples can include, but are not limited to, enzymes involved in glycogen, starch, and/or chrysolaminarin synthesis, including glucan synthases and branching enzymes. Additional or alternate examples can include enzymes involved in PHA biosynthesis, such as acetoacetyl-CoA synthase and/or PHA synthase.

Culturing the Microorganism

In some embodiments of the present invention, the microorganisms that produce free fatty acids can be cultured in a bioreactor. "Bioreactor" refers to an enclosure or partial enclosure in which cells are cultured, optionally in suspension and, when suspended, preferably in an aqueous liquid. The bioreactor can be used to culture microalgal cells through various phases of their physiological cycle. Bioreactors can offer many advantages for use in heterotrophic growth and propagation methods. To produce biomass for use in food, microorganisms are preferably fermented in large quantities in liquid, such as in suspension cultures as an example. Bioreactors such as steel fermentors can accommodate very large culture volumes (for example, ~40,000 liter and greater capacity bioreactors can be used in various embodiments of the invention). Bioreactors can additionally or alternatively typically allow for the control of one or more culture conditions, such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Cells can additionally or alternatively be cultured in a bioreactor equipped with an artificial light source, a "photobioreactor", and/or can have one or more walls that is transparent enough to light, including sunlight, to enable, facilitate, and/or maintain acceptable microorganism growth. For production of fatty acids, photosynthetic microorganisms can additionally or alternatively be cultured in shake flasks, test tubes, vials, microtiter dishes, petri dishes, or the like, or combinations thereof. Further additionally or alternatively, genetically engineered photosynthetic microorganisms may be grown in ponds, canals, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain $CO_2$ in addition to $CO_2$, it may be necessary to pretreat such sources such that the $CO_2$ level introduced into the (photo)bioreactor do not constitute a dangerous and/or lethal dose vis-à-vis the growth and/or survival of the microorganisms.

Substantially all or a portion of the fatty acids produced by the microorganism used in the methods disclosed herein may be released and/or secreted. In some embodiments, for example, at least 10 wt %, for example at least 20 wt %, at least 30 wt %, at least 40 wt %, or at least 50 wt %, of the free fatty acids produced by the microorganism can be released by the microorganism into the culture medium. In additional or alternate embodiments, for example, at least 10 wt %, for example at least 20 wt %, at least 30 wt %, at least 40 wt %, at least 50 wt %, at least 60 wt %, at least 70 wt %, at least 80 wt %, or at least 90 wt %, of the $C_8$ free fatty acids produced by the microorganism can be released by the microorganism into the culture medium. Further additionally or alternately, at least 10 wt %, for example at least 20 wt %, at least 30 wt %, at least 40 wt %, at least 50 wt %, at least 60 wt %, at least 70 wt %, at least 80 wt %, or at least 90 wt %, of the $C_{10}$ free fatty acids produced by the microorganism can be released by the microorganism into the culture medium. Still further additionally or alternately, at least 10 wt %, for example at least 20 wt %, at least 30 wt %, at least 40 wt %, at least 50 wt %, at least 60 wt %, at least 70 wt %, at least 80 wt %, or at least 90 wt %, of the $C_{12}$ and/or $C_{14}$ free fatty acids produced by the microorganism can be released by the microorganism into the culture medium. Yet further additionally or alternately, at least 10 wt %, for example at least 20 wt %, at least 30 wt %, at least 40 wt %, at least 50 wt %, at least 60 wt %, at least 70 wt %, at least 80 wt %, or at least 90 wt %, of the $C_{16}$ and/or $C_{18}$ free fatty acids produced by the microorganism can be released by the microorganism into the culture medium.

Fatty acids can be isolated from a culture of a microorganism that produces a free fatty acid in a medium that includes at least one carboxylate counterion source, such as, but not limited to, an alkaline earth metal ion source and a transition metal source, after one, for example after two, after three, after four, after five, after six, after seven, after eight, after nine, after ten, after eleven, after twelve, after thirteen, after fourteen, after fifteen, after sixteen, after seventeen, after eighteen, after nineteen, after twenty, after twenty-one, after twenty-two, after twenty-three, after twenty-four, after twenty-five, after twenty-six, after twenty-seven, after twenty-eight, after twenty-nine, after thirty, or after more than thirty days in culture. The free fatty acid can be harvested from the culture in continuous, semicontinuous, or batch mode. For example, the culture can be periodically "swept" or vacuumed with a device that collects the fatty acid-containing (semi-)solid components, e.g., from the surface of the media.

Fatty acids can be recovered from culture by recovery means known to those of ordinary skill in the art, such as by whole culture extraction, for example, using organic solvents. In some cases, recovery of fatty acids can be enhanced by homogenization of the cells, as provided in the examples herein. The recovery method can be adapted to efficiently recover only the released fatty acids, only the fatty acids produced and stored within the microorganisms, or both the produced and released fatty acids.

When free fatty acids are secreted/released into the culture medium by the microorganisms, the free fatty acids can be recovered in a variety of ways. At least a portion of the free fatty acids produced by the microorganism may be associated with the carboxylate counterion source, for example, as aggregates, particulates or as a film, gel, semi-solid, or solid that may be collected, scooped, skinned, or filtered from the culture medium. Alternatively or additionally, free fatty acids may be soluble in the culture medium. Straightforward isolation methods, e.g., by partition using immiscible solvents, may be employed. Additionally or alternatively, particulate adsorbents can be employed. These can include lipophilic particulates and/or ion exchange resins, depending on the design of the recovery method. They may be circulating in the separated medium and then collected, and/or the medium may be passed over a fixed bed column, for example a chromatographic column, containing these particulates. The fatty acids can then be eluted from the particulate adsorbents, e.g., by the use of an appropriate solvent. In such circumstances, one isolation method can include carrying out evaporation of the solvent, followed by further processing of the isolated fatty acids and lipids, to yield chemicals and/or fuels that can be used for a variety of commercial purposes.

In fatty acid production, the amount of the fatty acid produced and/or recovered by the methods described herein can advantageously be at least about 5 mg per liter of culture, for example at least about 7 mg per liter of culture, at least about 10 mg per liter of culture, at least about 15 mg per liter of culture, at least about 20 mg per liter of culture, at least about 25 mg per liter of culture, or at least about 50 mg per liter of culture. Although many times the goal can be to produce and/or recover as much fatty acid as possible, in some instances the amount of the fatty acid produced and/or recovered by the method described herein can be limited to about 5000 mg or less per liter of culture, for example about 2500 mg or less per liter of culture, about 2000 mg or less per liter of culture, about 1500 mg or less per liter of culture, about 1250 mg or less per liter of culture, about 1000 mg or less per liter of culture, about 900 mg or less per liter of culture, or about 800 mg or less per liter of culture.

Some embodiments of the present invention can include overexpressing an exogenous gene and/or an endogenous gene encoding a thioesterase and/or lipase in a microorganism by increasing the gene expression level of the exogenous gene and/or the endogenous gene and/or by increasing a produced amount of free fatty acids, compared to a microorganism in which the exogenous gene and/or the endogenous gene has not been introduced and/or has not been overexpressed. The microorganism is cultured in a medium that includes at least 0.5 mM of a carboxylate counterion source, such as, for example, a calcium or magnesium ion source. Additionally or alternatively, the free fatty acids produced by the microorganism overexpressing the exogenous gene and/or the endogenous gene can be released into the culture medium. Overexpressing an exogenous gene such as a thioesterase and/or lipase gene according to further embodiments can include expressing an exogenous thioesterase and/or lipase gene in a cell where the exogenous thioesterase and/or lipase was absent initially.

Additionally or alternatively, the present invention can include one or more of the following embodiments.

Embodiment 1

A method of culturing a microorganism that produces a free fatty acid in a culture medium comprising culturing the microorganism in the culture medium comprising at least about 0.5 mM of a carboxylate counterion source, where the carboxylate counterion source is any or a combination of a multivalent counterion source, a divalent counterion source, an alkaline earth metal ion source, or a transition metal ion source.

Embodiment 2

The method of Embodiment 1, in which at least 10 wt %, for example at least 20 wt %, at least 30 wt %, at least 40 wt %, or at least 50 wt %, of the free fatty acids produced by the microorganism are released by the microorganism into the culture medium.

Embodiment 3

The method of embodiment 1 or embodiment 2, in which the microorganism has a greater viability and/or a higher growth rate in the culture medium as compared with the microorganism in a culture medium comprising 0.25 mM or less of the carboxylate counterion source after one, for example after two, after three, after four, after five, after six, after seven, after eight, after nine, after ten, after eleven, after twelve, after thirteen, after fourteen, after fifteen, after sixteen, after seventeen, after eighteen, after nineteen, after twenty, after twenty-one, after twenty-two, after twenty-three, after twenty-four, after twenty-five, after twenty-six, after twenty-seven, after twenty-eight, after twenty-nine, after thirty, or after more than thirty, days in culture.

Embodiment 4

The method of any one of the previous embodiments, wherein the carboxylate counterion source comprises a calcium ion source and/or a magnesium ion source.

Embodiment 6

The method of any one of the previous embodiments, wherein the medium contains calcium and/or magnesium in an at least 2-fold the amount of a standard medium.

Embodiment 7

The method of any one of the previous embodiments, wherein the medium is a Fresh Water medium.

Embodiment 8

The method of any one of the previous embodiments, wherein the microorganism comprises an exogenous nucleic acid molecule encoding a thioesterase and/or a lipase.

Embodiment 9

The method of embodiment 8, wherein the thioesterase comprises or is an acyl-ACP thioesterase, an acyl-CoA thioesterase, a hydroxylbenzoyl-CoA thioesterase, or a combination thereof.

Embodiment 10

The method of embodiment 8 or embodiment 9, wherein the lipase is a member of the Pfam AB Hydrolase clan CL0028, such as an amino acid sequence that, when queried using Pfam HMM profiles, displays a Pfam match with any of Pfam 01674, Pfam 01764, Pfam 07819, Pfam 03583, and Pfam 00151 having an E-value parameter of 0.01 or less.

Embodiment 11

The method of any one of embodiments 8-10, wherein the microorganism further includes at least one non-native gene that encodes an enzyme on a fatty acid or lipid biosynthesis pathway, such as, for example, a gene encoding an acyl-CoA carboxylase and/or a ketoacyl-ACP synthase.

Embodiment 12

The method of any one of embodiments 8-11, wherein the microorganism further has attenuated expression of at least one gene that encodes an enzyme on a fatty acid and/or lipid biosynthesis pathway, such as, for example, a gene encoding an acyl-CoA synthetase, acyl-ACP synthetase, acyl-CoA dehydrogenase, glycerol-3-phosphate dehydrogenase, acetaldehyde-CoA dehydrogenase, pyruvate dehydrogenase, acetate kinase, or a combination thereof.

Embodiment 13

The method of any one of the previous embodiments, wherein the microorganism is a photosynthetic microorganism, such as a microalga or a cyanobacterium.

Embodiment 14

The method of embodiment 13, wherein the microalga is a species of one of the following genera: *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* and *Volvox,* and/or wherein the cyanobacterium is a species of one of the following genera: *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus*.

Embodiment 15

The method of any one of the previous embodiments, wherein the culture medium is a calcium-supplemented standard culture medium having the same composition as a standard culture medium with the exception that a greater amount of calcium is present in the calcium-supplemented culture medium with respect to the standard culture medium.

Embodiment 16

The method of any one of the previous embodiments, wherein at least one calcium salt is added to the standard culture medium, for example comprising calcium acetate, calcium carbonate, calcium chloride, calcium citrate, calcium gluconate, calcium hydroxide, calcium lactate, calcium nitrate, calcium phosphate, calcium sulfate, or a combination thereof.

Embodiment 17

The method of any one of the previous embodiments, wherein the microorganism is viable in a culture medium that comprises at least about 400 mg/L, for example at least about 800 mg/L, of free fatty acids and/or free fatty acid derivatives.

EXAMPLES

Example 1

Culturing Cyanobacterial Strains in the Presence of Free Fatty Acids

This example demonstrates that the presence of moderately high levels of free fatty acids in the growth medium can be toxic to a variety of cyanobacterial strains. The initial range of tolerance to free fatty acid was investigated by culturing *Synechocystis* sp. PCC 6803 in the presence of increasing amounts of free fatty acid using a mixture of $C_8$ to $C_{18}$ fatty acids. The mixture included about 15 wt % C8:0, about 15 wt % C10:0, about 15 wt % C12:0, about 15 wt % C14:0, about 15 wt % C16:0, about 15 wt % C16:1, about 5 wt % C18:0, and about 5 wt % C18:1 fatty acids. About two mL each of BG-11 medium (which includes approximately 0.25 mM calcium and approximately 0.3 mM magnesium, see Table 1) with 0, ~67.5 µg/mL, ~135 µg/mL, ~270 µg/mL, and ~540 µg/mL of the fatty acid mixture were cultured for about six days in the light with bubbled $CO_2$. FIG. 1 shows the culture tubes, in which the dark green color of culture tubes 1-3 that include 0, 67.5, and 135 µg/mL of the free fatty acids demonstrates dense growth of the algae at all three concentrations of free fatty acids, whereas tubes 4 and 5 that include 270 µg/mL, and 540 µg/mL of free fatty acids contain culture media that is colorless, indicating bleaching and lack of viability of the algal cells at these fatty acid concentrations. Thus, *Synechocystis* sp. PCC 6803 is able to tolerate ~135 µg/mL of the free fatty acid mixture but is not viable at concentrations of ~270 µg/mL and higher (bleached cultures).

TABLE 1

| BG-11 Medium (ATTC) | | | |
|---|---|---|---|
| NaNO₃ | | 1.5 g | |
| K₂HPO₄ | | 0.04 g | |
| MgSO₄ * 7H₂O | | 0.075 g | |
| CaCl₂ * 2H₂O | | 0.036 g | |
| Citric acid | | 6.0 mg | |
| Ferric ammonium citrate | | 6.0 mg | |
| EDTA | | 1.0 mg | |
| Na₂CO₃ | | 0.02 g | |
| Trace Metal Mix A5* | | 1.0 ml | |
| Agar (if needed) | | (up to) 10.0 g | |
| Distilled water | | 1.0 L | |
| *Trace Metal Mix A5 Composition | H₃BO₃ | 2.86 g | |
| | MnCl₂ * 4H₂O | 1.81 g | |
| | ZnSO₄ * 7H₂O | 0.22 g | |
| | Na₂MoO₄ * 2H₂O | 0.39 g | |
| | CuSO₄ * 5H₂O | 0.080 g | |
| | Co(NO₃)₂ * 6H₂O | 49.4 mg | |
| | Distilled water | to 1.0 L | |

The free fatty acid tolerance limit was also investigated for two isolated strains of *Synechococcus* and found to be in the range from about 100 mg/L to about 150 mg/L for SGI-004 (WT-SG I-E-0071) and from about 150 mg/L to about 200 mg/L for SGI-272 (WT-SGI-E-0077). In this experiment, cells were cultured for about three days in about 1 mL each of BG-11 media that included 0, ~50 mg/L, ~100 mg/L, ~150 mg/L, ~200 mg/L, and ~500 mg/L, of free fatty acid.

Example 2

This Example demonstrates that free fatty acids can be toxic to a wide range of cyanobacteria, and that calcium is able to alleviate the effects of free fatty acids. In addition, fifteen strains of cyanobacteria isolated from environmental samples from various locations in the states of California and Texas, including both salt water and fresh water environments, were tested for tolerance to free fatty acids. The cyanobacterial strains were cultured in BG-11 media at normal (~1×) and increased (~10×) calcium concentrations. For ~10× calcium-enhanced media, the additional calcium was added as calcium chloride ($CaCl_2$). In these tests, ~1 ml each of fresh cyanobacterial culture (~0.3 OD) was added to each well of a 24-well plate. The culture medium was either standard BG-11, or BG-11 with the addition of calcium to a concentration ten fold (10×) the BG-11 standard concentration (about 2.5 mM). The total concentrations of free fatty acids ($C_{14}$ and $C_{16}$) added to the wells were 0, ~50 mg/L, ~100 mg/L, ~200 mg/L, ~400 mg/L, and ~800 mg/L. The ratio of $C_{14}$:$C_{16}$ free fatty acids was about 2:3. After about 3 days of shaking (at about 30° C., ~50 µE/m²/s, and about 145 rpm), the cells were suspended for visually assessing the viability of the individual cultures. For each strain, the highest concentration of free fatty acids that allowed growth of cyanobacterial cells was recorded (Table 2). Addition of ~10 fold of additional calcium substantially improved the fatty acid tolerance for all of cyanobacteria strains tested (Table 2).

TABLE 2

Tolerance of cyanobacterial strains to free fatty acids in the presence of ~0.25 mM and 2.5 mM calcium in the media

| Strain ID | Most Closely-Related Organism | FFA mg/L Tolerance at 1 × Calcium | FFA mg/L Tolerance at 10 × Calcium |
|---|---|---|---|
| PH-00071 | *Synechocystis* PCC 6803 | 200 | 800 |
| WT-SGI-E-00068 | *Synechocystis* sp. | 50 | 800 |
| WT-SGI-E-00070 | *Phormidium* sp. | 200 | 800 |
| WT-SGI-E-00071 | *Synechococcus elongatus* | 200 | 800 |
| WT-SGI-E-00072 | *Chroococcidiopsis* sp. | 0 | 200 |
| WT-SGI-E-00073 | *Chroococcidiopsis* sp. | 0 | 200 |
| WT-SGI-E-00074 | *Leptolyngbya antarctica* | 100 | 400 |
| WT-SGI-E-00075 | *Synechococcus* sp. BD-1 | 100 | 400 |
| WT-SGI-E-00076 | *Synechococcus* sp. BD-1 | 0 | 400 |
| WT-SGI-E-00077 | *Synechococcus elongatus* | 0 | 200 |
| WT-SGI-E-00078 | *Cyanobacterium aponinum* | 50 | 400 |
| WT-SGI-E-00079 | *Cyanobacterium* sp. | 0 | 400 |
| WT-SGI-E-00080 | *Synechococcus elongatus* | 50 | 400 |
| WT-SGI-E-00081 | *Synechocystis* sp. | 50 | 400 |
| WT-SGI-E-00082 | *Synechococcus lividus* | 0 | 400 |
| WT-SGI-E-00083 | Aggregate forming unicellular cyanobacteria | 0 | 400 |

Example 3

This Example demonstrates that elevated concentrations of calcium or magnesium can reduce the toxicity of free fatty acids in the media. The *Synechocystis* sp. PCC 6803 strain and the SGI-004 *Synechococcus* strain were both tested to see if calcium and/or magnesium could alleviate the toxic effects of free fatty acid in the media. BG-11 media was used to culture the cells in multiwall plates. Calcium ($CaCl_2$) and magnesium ($MgCl_2$) were added alone and in combination to achieve a concentration two-fold (2×) and four-fold (4×) that of standard BG-11 media. The results show that increasing both calcium and magnesium in the media increased free fatty tolerance in *Synechocystis* sp. PCC 6803. (Table 3). Only calcium increased free fatty acid tolerance in the SGI-004 *Synechococcus* strain (Table 4); magnesium had no discernible protective effect on the viability of this strain at the concentrations tested. At a concentration double that of the BG-11 recipe (approximately 0.5 mM), calcium added a tolerance of up to about 100 mg/L more of free fatty acid for both of the strains.

TABLE 3

Tolerance of *Synechocystis* sp. PCC 6803 to free fatty acids in the presence of increased amounts of calcium and magnesium

| Media | concentration of free fatty acid in mg/L | | | | | |
|---|---|---|---|---|---|---|
| | 0 | 100 | 200 | 250 | 300 | 500 |
| BG-11 | + | + | + | − | − | − |
| Ca 2X | + | + | + | + | + | − |
| Mg 2X | + | + | + | + | + | − |
| Ca/Mg | + | + | + | + | + | − |
| Ca 4X | + | + | + | + | + | − |
| Mg 4X | + | + | + | + | + | − |
| Ca/Mg | + | + | + | + | + | − |

TABLE 4

Tolerance of *Synechococcus* to free fatty acids in the presence of increased amounts of calcium and magnesium

| Media | concentration of free fatty acid in mg/L | | | | | |
|---|---|---|---|---|---|---|
| | 0 | 100 | 200 | 250 | 300 | 500 |
| BG-11 | + | + | − | − | − | − |
| Ca 2X | + | + | + | + | − | − |
| Mg 2X | + | + | − | − | − | − |
| Ca/Mg | + | + | + | − | − | − |
| Ca 4X | + | + | + | + | + | − |
| Mg 4X | + | + | − | − | − | − |
| Ca/Mg | + | + | + | + | + | − |

The benefit of calcium can be extended to relatively high levels of free fatty acid in the media. At roughly twelve times the concentration of calcium in media (relative to a standard medium, such as BG-11), e.g., at about 3 mM calcium, the *Synechocystis* sp. PCC 6803 strain can tolerate at least ~800 mg/L of free fatty acid. As shown in Table 5, higher levels of calcium can provide increased free fatty acid tolerance in *Synechocystis* sp. PCC 6803. Four times the BG-11 calcium, or about 1 mM calcium, increases viability of *Synechocystis* in the presence of 400 mg/L fatty acids, while eight times the BG-11 calcium content (or about 2 mM calcium) allows for viability in the presence of up to 400 mg/L fatty acids, and twelve times the BG-11 calcium content (or about 3 mM calcium) allows the cells to survive having at least 800 mg/L fatty acids in the culture medium.

TABLE 5

Increased tolerance of *Synechocystis* sp. PCC 6803 to free fatty acids in the presence of increased amounts of calcium

| Media | concentration of free fatty acid in mg/L | | | | | |
|---|---|---|---|---|---|---|
| | 0 | 200 | 400 | 600 | 800 | 1000 |
| BG-11 | + | + | − | − | − | − |
| Ca 4X | + | + | + | − | − | − |
| Ca 8X | + | + | + | + | − | − |
| Ca 12X | + | + | + | + | + | − |

For large-scale production of fatty acids, calcium (and/or magnesium) supplementation would allow for fatty acids to accumulate during a production phase to be harvested one or more times in a non-continuous mode. Calcium concentrations up to about one hundred times the concentration of calcium in standard BG-11 medium (that is, up to ~25 mM) have been tested on *Synechocystis* sp. PCC 6803, with no growth defects exhibited by the cyanobacteria grown in the calcium-enhanced media.

Example 4

Figure 2A:
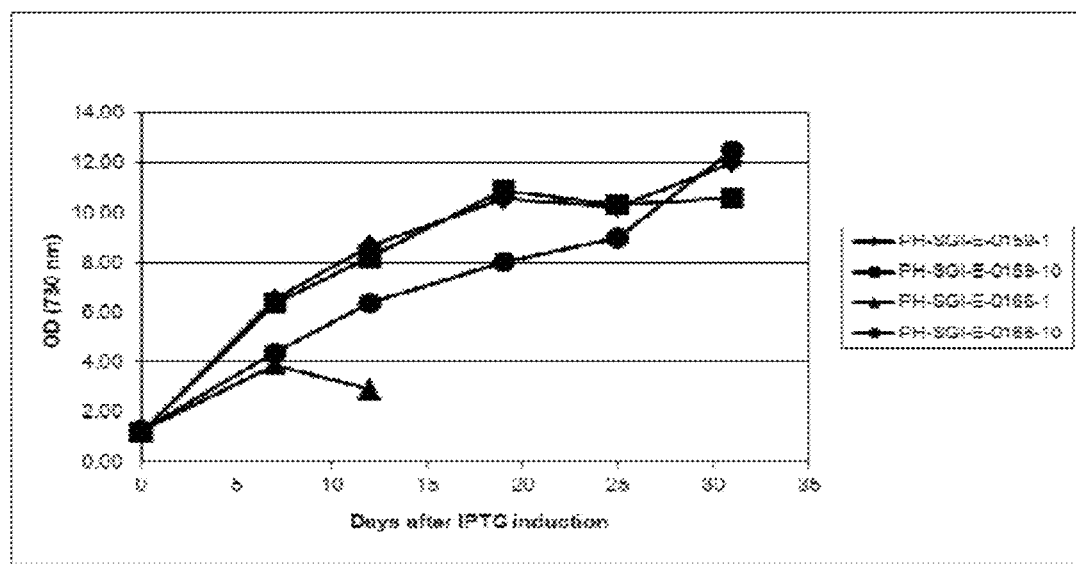
FIG. 2a is a graph showing the post-IPTG induction growth of cultures (as measure by OD at 730 nm) of *Synechocystis* PCC 6803 transformed with one (PH-SGI-E-0159-1; "159") or three (PH-SGI-E-0166-1; "166") copies of the Cc1FatB1 *Cuphea carthagenensis* acyl-ACP thioesterase (diamonds, strain 159 in standard BG-11 media; squares, strain 159 in standard BG-11 media supplemented to 10-fold the amount of calcium of BG-11 (~2.5 mM); triangles, cyanobacterial strain 166 in standard BG-11 media; circles, strain 166 in standard BG-11 media supplemented to 10-fold the amount of calcium of BG-11 (~2.5 mM)).
Figure 2B:
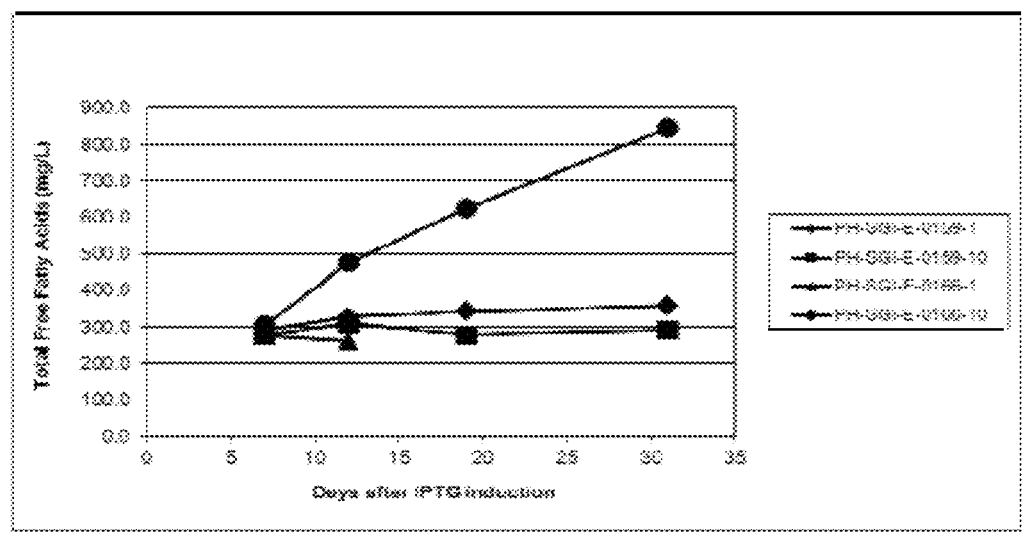
FIG. 2b is a graph showing the post-IPTG induction free fatty acid production in mg/L of cultures of *Synechocystis* strains transformed with one (PH-SGI-E-0159-1; "159") or three (PH-SGI-E-0166-1; "166") copies of the Cc1FatB1 *Cuphea carthagenensis* acyl-ACP thioesterase (diamonds, strain 159 in standard BG-11 media; squares, strain 159 in standard BG-11 media supplemented to 10-fold the amount of calcium of BG-11 (~2.5 mM); triangles, cyanobacterial strain 166 in standard BG-11 media; circles, strain 166 in standard BG-11 media supplemented to 10-fold the amount of calcium of BG-11 (~2.5 mM)).
Figure 2C:
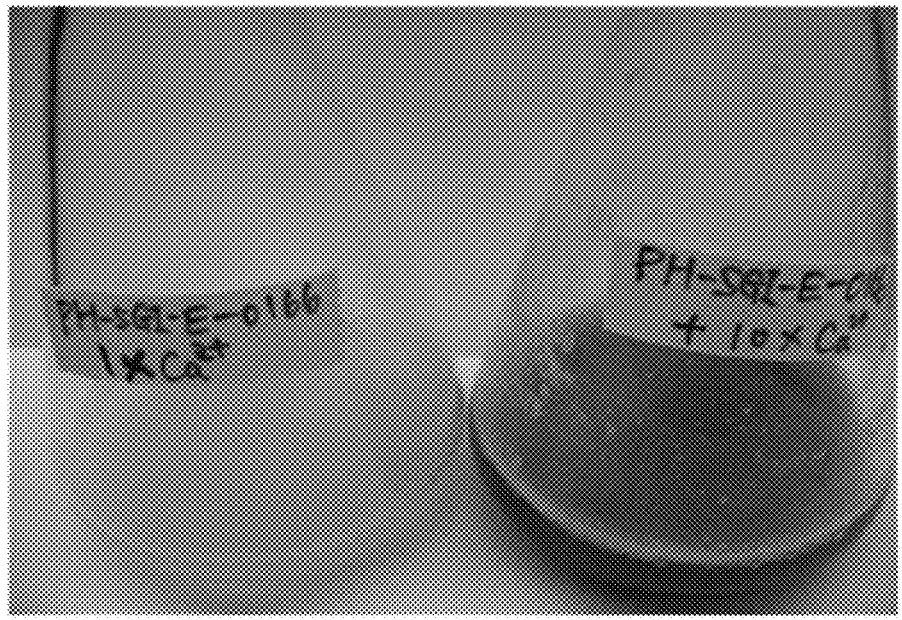
FIG. 2c shows an image of cultures of the *Synechocystis* sp. 3-copy-Cc1FatB1 strain (PH-SGI-E-0166-1; "166") at day 12 of growth in BG-11 media without calcium supplementation (leftmost flask, showing a bleached culture) and with BG-11 media including about 10-fold the standard concentration of calcium (rightmost flask, showing dense growth of the cyanobacterial culture).

This example demonstrates the long-term effect of calcium addition on a *Synechocystis* strain that expresses an exogenous acyl-ACP thioesterase for the production of free fatty acids. Cultures of a *Synechocystis* sp. PCC 6803 strain that included one copy of the *Cuphea carthagenensis* Cc1FatB1 acyl-ACP thioesterase (PH-SGI-E-0159), with or without extra calcium addition, continued to grow and stayed green for at least 31 days and produced about 300-350 mg/L free fatty acids. The 3-copy thioesterase strain (PH-SGI-E-0166) without extra calcium feeding completely bleached after ~12 days of IPTG induction; whereas its cognate culture with ~10× calcium concentration survived and accumulated about 940 mg/L total free fatty acids after about 31 days of IPTG induction (FIG. 2). The data suggests that addition of excess amounts of calcium improved the long-term stability, viability, and robustness of *Synechocystis* strains producing relatively high concentrations of fatty acids. White deposits floating on the surface of the surviving microorganism culture are presumed to be calcium soap scum resulting from free fatty acid(s) complexing with the excess calcium.

Cloning Details

The PH-SGI-E-0159 strain was developed by introducing pSGI-TW01 (SEQ ID NO:1) into *Synechocystis* sp. PCC 6803. This vector enables intergration of a Cc1FatB1 acyl-ACP thioesterase gene expression cassette into the RS2 integration site. The PH-SGI-E-0166 strain was developed by introducing pSGI-TW01 (SEQ ID NO:1), pSGI-KF01 (SEQ ID NO:2), and pSGI-TW03 (SEQ ID NO:3), each of which included a Cc1FatB1 acyl-ACP thioesterase gene expression cassette into *Synechocystis* sp. PCC 6803 for integration of the expression cassettes into the RS2, RS1, and RS3 integration sites, respectively.

The protein-encoding sequence of the Cc1fatB1 gene from *Cuphea carthagenensis* was used to design a nucleotide sequence that conformed to the codon preference of *Synechocystis* sp. PCC 6803. The nucleotide sequences of the codon-optimized Cc1fatB1 gene, encoding an acyl-ACP thioesterase having a truncated chloroplast transit peptide) is provided as SEQ ID NO:4 and the amino acid sequence is provided as SEQ ID NO:5.

The pSGI-KF01 thioesterase construct was cloned by inserting a copy of the Cc1fatB1 coding sequence into a RS1 integration shuttle vector. The Cc1FatB1 codon-optimized coding sequence was amplified by primers YC-244 (CAC-TAAGGAGGAAAAAAACCATGGCGAACGG-TAGCGCTGTC; SEQ ID NO:6) and YC-248 (TACCATAT-GCATGCGAGCTCACTATTAACTGGCGGGATTACCAT-TACTGG; SEQ ID NO:7) from plasmid pSG1-GltrcE-GLA148 (PE-0421) that included the synthetic codon-optimized Cc1fatB1 gene. The YC-244 primer included an NcoI restriction site, and the YC-248 primer included a SacI restriction site. Both the PCR fragment and the RS1 vector were restriction digested with NcoI and SacI, and then ligated together to construct pSG1-KF01.

The RS1 vector was constructed by inserting the RS1 sequences into pUC118, which enables transformation of *Synechocystis* sp. PCC 6803 via double homologous recombination-mediated integration into the "RS1" site of the chromosome (Williams (1988) *Methods Enzymol.,* 167:766-778). The pUC118 vector was digested with HindIII and EcoRI to remove the multiple cloning site (MCS) sequence, and then blunted with T4 DNA polymerase. The RS1 upstream (RS1-up) and downstream (RS1-down) fragments were amplified from *Synechocystis* genomic DNA by the following primer pairs: for RS1-up, the primers RS6803-5 (attgctgaagcggaatc-cctg; SEQ ID NO:8) and RSMCS-3 (catggagatctgagctcgcat-gcatatggtaccatataaccatcaaagccatagttgg; SEQ ID NO:9) were used, and, for RS1-down, the primers RSMCS-5 (atatgcatgc-gagctcagatctccatggaattcggtaccggtatggatg acaccgatg; SEQ ID NO:10) and RS6803-3 (tgggggaccattctctggatc; SEQ ID NO:11) were used. The complete RS1 sequence was re-amplified by the end primers, RS6803-5 (SEQ ID NO:8) and RS6803-3 (SEQ ID NO:11), using the RS1-up and RS1-down fragments as the templates. The re-amplified 2-kb RS1 complete sequence was then ligated into the pUC118 backbone to make pSGI-YC02. A DNA fragment carrying the kanamycin resistance gene and the rrnB terminator, 1579-KmR, that was amplified by primers NS2-5MCS (gcatgcgagctcagatctaccag-gttgtccttggcgcag; SEQ ID NO:12) and NS21-3MCS (ccatac-cggtaccgaattcgccacgttactgctcgatgg; SEQ ID NO:13), was inserted between EcoRI and BglII sites on pSGI-YC02. An EcoRI fragment containing the lacIq gene was inserted into the EcoRI site of the pSGI-YC02 RS1 vector, between the RS1-down sequence and the 1579-KmR fragment. The trcY promoter (SEQ ID NO:14) was amplified with the primers 4YC-trcY-5 (actagtcctgaggctgaaatgagctgt-tgacaattaatcatccggctcgtataatgtgtggaattgtgag; SEQ ID NO:15) and 4YC-trcY-3 (ccatggtttttttcctccttactct-caaattgttatccgctcacaattccacacattatacgaccggat; SEQ ID NO:16) and was inserted between SpeI and NcoI sites of the RS1 vector to allow for regulation using this IPTG-inducible promoter.

The resulting RS1 integration vector for expression of the Cc1fatB1 gene, pSGI-KF01, is provided as SEQ ID NO:2.

The pSGI-TW01 thioesterase construct (SEQ ID NO:1) was cloned by inserting a copy of Cc1fatB1 gene (SEQ ID NO:4) into a RS2 shuttle vector.

The RS2 integration shuttle vector was based on a pUC19 backbone that included a bacterial origin of replication for maintenance of the plasmid in *E. coli*. The RS2 vector was constructed to include the RS2 "up" and "down" sequences from the *Synechocystis* genome for homologous recombination. This vector also included an Omega-Sp cassette providing streptomycin/spectinomycin resistance, and the IPTG-inducible trcY promoter. To create the RS2 expression vector, the RS2 sequence (including both the up and down fragments) was amplified from *Synechocystis* PCC 6803 genomic DNA using primers: RS2-5 (gggcccctatttgcccgtattctgccctatcc; SEQ ID NO:17) and RS2-3 (gggcccgactgcctttggtggtattac-cgatg; SEQ ID NO:18). Plasmid pUC19 was digested with HindIII and EcoRI to remove the multiple cloning site (MCS), and then treated with T4-DNA polymerase to blunt the ends. The RS2 sequence (comprising RS2 up and RS2 down; ~1.8 kb) was ligated into the pUC19 backbone. The resulting plasmid was named pYC34. The pYC34 plasmid was then digested with BglII, which cut within the RS2 sequence, opening up the integration site. A copy of the Omega-Sp cassette (BamHI fragment) was ligated into the BglII site of pYC34 to make pYC36. The pYC36 plasmid was digested with FspI to remove the majority of the Ampicillin resistance gene (Apr), making spectinomycin/ streptomycin the only selection marker in the plasmid. The constructed plasmid was named pYC37. An EcoRI fragment containing the lacIq gene was inserted into the EcoRI site of pYC37, between the RS2-up sequence and the Omega-Sp cassette to allow for regulation of IPTG-inducible promoters. The vector further included a trcY promoter. The trcY promoter (SEQ ID NO:14) was amplified as for the RS1 integration vector, using the 4YC-trcY-5 (SEQ ID NO:15) and 4YC-trcY-3 (SEQ ID NO:16) primers. The PCR amplified trcY promoter sequence (SEQ ID NO:14) was inserted between the SpeI and NocI sites on the RS2 vector.

The Cc1fatB1 coding sequence was amplified by primers YC-244 (SEQ ID NO:6), which included a terminal NcoI site, and YC-245 (AAAGCTTAGGCCTGCAGATATCTAGAT-TAACTGGCGGGATTACCATTACTGG; SEQ ID NO:19), which included a terminal XbaI site, from plasmid pSGI-GLtrcE-GLA 148 (PE-0421) that contained the synthetic, N-terminally truncated, codon-optimized Cc1fatB1 gene (SEQ ID NO:4). The PCR fragment was restriction digested with NcoI and XbaI, and then ligated 10 the vector backbone using the NcoI and XbaI sites of the vector to create pSGI-TW01 (SEQ ID NO:1).

Construct pSGI-TW03 (SEQ ID NO:3), having the Cc1FatB1 thioesterase gene in an RS3 integration site vector, was cloned by inserting a copy of trcY::Cc1FatB1 cassette into the RS3 shuttle vector pSGI-NB5. The construction details of pSGI-NB5 are as follows:

A DNA fragment having a size of approximately 1.7-kbp and spanning an area upstream and into the coding region of the acyl-ACP synthetase-encoding gene, slr1609 (Accession BAA17024.1 GI:1652099), from *Synechocystis* sp. PCC 6803 was amplified from genomic DNA using PCR with primers NB001 (CTCGAGCCCCCGTGCTATGACTAGC; SEQ ID NO:20) and NB002 (CTCGAGCG-GAACGTTTTTTGTACCCC; SEQ ID NO:21). This fragment (the RS3 site sequence) was cloned into the pCR2.1 vector (Invitrogen) to yield plasmid pSGI-NB3 and subsequently cut with the restriction enzyme Mfe1. A chloramphenicol resistance marker cassette containing the cat gene and associated regulatory control sequences was amplified from plasmid pAM1573 (Andersson, et al., Methods Enzymol. 2000, 305:527-542) to contain flanking Mfe1 restriction sites using PCR with primers NB010 (CAATTGGTCA-CACGGGATAATACCGCGCC; SEQ ID NO:22) and NB011 (CAATTGGTCGATCATATCGTCAATTATTACCTCCAC; SEQ ID NO:23). The cat gene expression cassette was then inserted into the Mfe1 site of pSGI-NB3 to yield pSGI-NB5.

To insert the Cc1FatB1 thioesterase gene plus trcY promoter into pSGI-NB5, primers YC-253 (GCTTCTCAAAT-GCCTGAGGTATACTGAAATGAGCTGTTGA CAAT-TAATC; SEQ ID NO:24) and YC-254 (TGAGCAAACTGGCCTCAGGAT CGGGCCTGGCAC-CCAG; SEQ ID NO:25) were used to amplify the trcY::Cc1FatB1 cassette using RS2 integration construct pSGI-TW01 (SEQ ID NO:1) as the PCR template. The pSGI-NB5 vector was cut open with Bsu36I, and the PCR fragment was inserted using a BPS cloning kit.

Synechocystis sp. PCC 6803 cells were transformed according to established protocols (Zang et al. (2007) J. Microbiology 45:241-245) and plated on BG-11 agar plates containing appropriate antibiotics to select for transformants. Resulting colonies were tested for the presence of the acyl-ACP thioesterase gene and segregation of chromosomes by PCR. The following antibiotics were used: chloramphenicol 20 mg/L, kanamycin 20 mg/L, and streptomycin 20 mg/L.

Synechocystis sp. PCC6803 (nontransformed) and Synechocystis sp. PCC6803 transformed with three copies of the Cc1FatB1 Cupea cathagenensis acyl-ACP thioesterase. For each strain, 20 ml fresh culture (~1.0 OD730) plus 1 mM IPTG (final concentration) was inoculated into 125-ml glass flasks, and excess amount of calcium was added to the proper flasks with a final concentration of 11 fold of that in BG-11. For strain 159 flasks, 20 mg/L streptomycin was added; for strain 166, 10 mg/L kanamycin, 10 mg/L streptomycin, and 10 mg/L chloramphenicol was added for selection. The flasks were growing for 31 days in the shaker (Innova 4230, New Brunswick; 145 rpm) at 30° C. and approximately 50 µE/m2/s, with a constant supply of 1% $CO_2$. For sample collection, the flasks were shaken vigorously for 10 seconds to homogenize the culture, 0.6 ml culture was then collected from each flask by pipetting and transferred into GC vials and saved at −20° C. The time points were day-7, day-12, day-19 and day-31 after IPTG induction. After each sample collection, 5 ml fresh BG-11 media plus 1 mM IPTG were replenished into each flask; 10 fold of calcium was also added to the proper flasks. At the end of the experiments, the collected samples were submitted for GC-Free fatty acids analysis Addition of calcium helps the long-term stability and robustness of fatty-acids producing strains.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference in their entireties.

Nucleic acid and amino acid sequences identified by Accession Numbers or GenInfo Identifiers are also incorporated by reference herein. Accession numbers are unique identifiers for a sequence record publicly available at the National Center for Biotechnology Information internet site maintained by the United States National Institutes of Health which can be accessed at ncbi.nlm.nih.gov. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appeared in a specific Genbank record. Searching and obtaining nucleic acid or gene sequences or protein sequences based on Accession numbers and GI numbers is well known in the arts of cell biology, biochemistry, molecular biology, and molecular genetics.

It must also be noted that as used herein and in the appended claims, the singular forms "a," "and" and "the" include plural referents unless the context clearly dictates otherwise. The use of "or" in a listing of two or more items indicates that any combination of the items is contemplated, for example, "A or B" indicates that A alone, B alone, or both A and B are intended. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

What is claimed is:

1. A method of improving the viability of a cultured photosynthetic microorganism in a medium containing a high level of free fatty acid, the method comprising culturing a photosynthetic microorganism that comprises a non-native nucleic acid sequence encoding a thioesterase or a non-native nucleic acid sequence encoding a polypeptide having lipolytic activity in a culture medium comprising a high level of free fatty acid and at least about 1 mM of a carboxylate counterion source selected from the group consisting of calcium, magnesium, and a combination of calcium and magnesium.

2. The method of claim 1, wherein the photosynthetic microorganism releases at least one free fatty acid into the culture medium.

3. A method of improving the viability of a cultured photosynthetic microorganism in a medium containing a high level of free fatty acid, the method comprising culturing a photosynthetic microorganism that comprises a non-native nucleic acid sequence encoding a thioesterase or a non-native nucleic acid sequence encoding a polypeptide having lipolytic activity in a culture medium comprising a high level of free fatty acid and at least about 1 mM of a carboxylate counterion source selected from the group consisting of calcium, magnesium, and a combination of calcium and magnesium, wherein the culture medium comprises at least 0.5 mM calcium.

4. The method of claim 1, wherein the medium contains at least 2 mM of calcium, magnesium, or a combination thereof.

5. The method of claim 1, wherein the photosynthetic microorganism is a microalga.

6. The method of claim 5, wherein the microalga is selected from a group consisting of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, and *Volvox*.

7. The method of claim 1, wherein the photosynthetic microorganism is a *cyanobacterium*.

8. The method of claim 7, wherein the cyanobacterium is selected from a group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, and *Xenococcus*.

9. The method of claim 1, further comprising isolating one or more free fatty acids from the photosynthetic microorganism, the culture medium, or a combination thereof.

10. The method of claim 3, wherein the culture medium is a calcium-supplemented culture medium having substantially the same composition as a standard culture medium, with exception that a greater amount of calcium is present in the calcium-supplemented culture medium than is present in the standard culture medium.

11. The method of claim 10, wherein there is at least twice the amount of calcium present in the calcium-supplemented culture medium as is present in the standard culture medium.

12. The method of claim 1, wherein the culture medium does not comprise a substantial amount of a reduced carbon source.

13. The method of claim 12, wherein the culture medium comprises an inorganic carbon source.

14. The method of claim 1, wherein the high level of free fatty acid is at least 400 mg/L.

15. The method of claim 1, wherein the improvement in viability is measured against a control comprising the cultured photosynthetic microorganism in substantially the same medium except the medium comprises about 0.25 mM or less of a carboxylate counterion.

16. The method of claim 15, wherein the improvement in viability is determined by measuring the number of days before visible bleaching of the culture and/or by measuring the number of days without a decline in cell count or optical density with respect to the control.

17. The method of claim 16, wherein the improvement in viability consists of an ability to grow to an $OD_{730\ nm}$ of at least 4.

18. The method of claim 16, wherein the improvement in viability consists of an ability to grow for three days without visible bleaching.

* * * * *

SEQUENCE LISTING

```
<160> NUMBER OF SEQ ID NOS: 25

<210> SEQ ID NO 1
<211> LENGTH: 8004
<212> TYPE: DNA
<213> ORGANISM: Artificial Sequence
<220> FEATURE:
<223> OTHER INFORMATION: pSGI-TW01 plasmid sequence

<400> SEQUENCE: 1
gtctgacgct cagtggaacg aaaactcacg ttaagggatt ttggtcatga gattatcaaa      60
aaggatcttc acctagatcc tttaaatta aaaatgaagt tttaaatcaa tctaaagtat     120
atatgagtaa acttggtctg acagttacca atgcttaatc agtgaggcac ctatctcagc     180
gatctgtcta tttcgttcat ccatagttgc ctgactcccc gtcgtgtaga taactacgat     240
acgggagggc ttaccatctg gccccagtgc tgcaatgata ccgcgagacc cacgctcacc     300
ggctccagat ttatcagcaa taaaccagcc agccggaagg gccgagcgca gaagtggtcc     360
tgcaacttta tccgcctcca tccagtctat taattgttgc cgggaagcta gagtaagtag     420
ttcgccagtt aatagtttgc gcaactgttg ggaagggcga tcggtgcggg cctcttcgct     480
attacgccag ctggcgaaag ggggatgtgc tgcaaggcga ttaagttggg taacgccagg     540
gtttttccag tcacgacgtt gtaaaacgac ggccagtgaa ttgggcccga ctgcctttgg     600
```

```
tggtattacc gatgagtggc acgttatttt caccgctctg gccgtgttga gcatggtgct    660
gggcaacgtg gtggctttag cccaaaccag catgaaacgg atgttggcct actcttccat    720
cggtcaagca ggctttgtga tgattggcct agtggccggc agtgaagatg gttacgccag    780
catggttttc tacatgctca tctatctgtt tatgaacctg ggggcgttta gttgcattat    840
tctcttcacc ctccgcactg gcagtgacca aattagtgat tacgctggtc tgtaccacaa    900
agaccccttg ttaaccttgg gcttgagcat ttgtttatta tccttggggg gcattcctcc    960
tctggcgggc ttttcggca aaatttacat cttctgggcc ggttggcaat cgggattgta   1020
tggcctagtc ctacttggtc tggttaccag tgtagtttcc atctactact acatccgggt   1080
ggtgaaaatg atggtggtga aggagcccca ggaaatgtcc gaagtaatca aaaattaccc   1140
ggccatcaaa tggaatttac ccggcatgcg tcccctacag gtgggcattg tcgctacttt   1200
ggttgctacc tcgctggcag gtattctggc taatcccctc tttaacctcg ccaccgattc   1260
cgtggtcagc accaagatgt tgcagacagc cctccagcaa acaggagaaa ctccggcgat   1320
cgccatttcc catgatttac cctaggggta tcaggaaata ttgctttgca ggcaaaagcc   1380
aatgagtgta actatagaaa ccgatttaaa ggagatccac tagtcctgag gctgaaatga   1440
gctgttgaca attaatcatc cggctcgtat aatgtgtgga attgtgagcg ataacaatt    1500 tcacactaag gaggaaaaaa accatggcga acgtagcgc tgtctctctg aagagcggct   1560
ccttgaatac gcaagaggac acttcttctt ccccaccgcc acgcgcgttc atcaaccaat   1620
tacccgactg gtccatgtta ttgacggcga ttaccactgt ctttgttgcc gcagagaaac   1680
agtggactat gttagaccgc aagagcaagc gctccgatat gttagtggat tcttttggca   1740
tggaacgcat tgtgcaggat ggcttagtgt ttcgtcaatc ttttagcatt cgttcttatg   1800
aaatcggtgc agatcgtcgt gcatccattg aaaccttaat gaaccatctg caggaaacta   1860
gcttgaatca ttgcaaatcc attcgcttgt tgaatgaggg ttttggtcgc acccccgaga   1920
tgtgcaaacg tgacttgatc tgggtggtta cccgcatgca catcatggtc aaccgctacc   1980
ctacctgggg tgataccgtt gagattaaca cttgggtttc ccaaagcggc aagaatggta   2040
tgggtcgtga ttggctgatt tccgactgta ataccggcga atcctgatc cgcgcgacgt   2100 ctgcatgggc gatgatgaac caaaagaccc gtcgtctgtc taaactgcct tacgaagtca   2160
gccaagagat tgctccgcac ttcgtcgaca gccctcccgt gatcgaggac ggcgaccgta   2220
agttacacaa gttcgatgtg aaaaccggcg acagcatccg taaaggtttg actccgcgtt   2280
ggaatgactt agatgttaat cagcacgtta acaacgttaa gtatatcggc tggatcttag   2340
agagcatgcc gaccgaggtc ttggaaactc atgaactgtg tttcttaact ctggagtatc   2400
gtcgcgagtg cggtcgcgat agcgtgctgg aatctgtgac cgcgatggat ccttctaatg   2460
aaggtggtcg ctcccactac cagcatttac tgcgcttgga ggacggtact gacatcgtta   2520
agggccgcac tgagtggcgt ccaaagaatg cccggaatat tggtgccatt agtaccggta   2580
aaaccagtaa tggtaatccc gccagttaat ctagatatct gcaggcctaa gctttatgct   2640
tgtaaaccgt tttgtgaaaa aatttttaaa ataaaaaagg ggacctctag ggtccccaat   2700
taattagtaa tataatctat taaaggtcat tcaaaaggtc atccaccgga tcaattcccc   2760
tgctcgcgca ggctgggtgc caggcccgat ccttggagcc cttgccctcc cgcacgatga   2820
tcgtgccgtg atcgaaatcc agatccttga cccgcagttg caaacccctca ctgatccgca   2880 tgcccgttcc atacagaagc tgggcgaaca acgatgctc gccttccaga aaaccgagga   2940
```

```
tgcgaaccac ttcatccggg gtcagcacca ccggcaagcg ccgcgacggc cgaggtcttc      3000
cgatctcctg aagccagggc agatccgtgc acagcacctt gccgtagaag aacagcaagg      3060
ccgccaatgc ctgacgatgc gtggagaccg aaaccttgcg ctcgttcgcc agccaggaca      3120
gaaatgcctc gacttcgctg ctgcccaagg ttgccgggtg acgcacaccg tggaaacgga      3180
tgaaggcacg aacccagtgg acataagcct gttcggttcg taagctgtaa tgcaagtagc      3240
gtatgcgctc acgcaactgg tccagaacct gaccgaacg cagcggtggt aacgcgcag       3300 tggcggtttt catggcttgt tatgactgtt tttttggggt acagtctatg cctcggtcgg      3360
gcatccaagc agcaagcgcg ttacgccgtg ggtcgatgtt tgatgttatg gagcagcaac     3420
gatgttacgc agcagggcag tcgccctaaa acaaagttaa acatcatgag ggaagcggtg     3480
atcgccgaag tatcgactca actatcagag gtagttggcg tcatcgagcg ccatctcgaa      3540
ccgacgttgc tggccgtaca tttgtacggg tccgcagtgg atggcggcct gaagccacac     3600
agtgatattg atttgctggt tacggtgacc gtaaggcttg atgaaacaac gcggcgagct      3660
ttgatcaacg accttttgga aacttcggct tcccctggag agagcgagat tctccgcgct    3720
gtagaagtca ccattgttgt gcacgacgac atcattccgt ggcgttatcc agctaagcgc     3780
gaactgcaat ttggagaatg gcagcgcaat gacattcttg caggtatctt cgagccagcc    3840
acgatcgaca ttgatctggc tatcttgctg acaaaagcaa gagaacatag cgttgccttg    3900
gtaggtccag cggcggagga actctttgat ccggttcctg aacaggatct atttgaggcg   3960
ctaaatgaaa ccttaacgct atggaactcg ccgcccgact gggctggcga tgagcgaaat   4020
gtagtgctta cgttgtcccg catttggtac agcgcagtaa ccggcaaaat cgcgccgaag   4080
gatgtcgctg ccgactgggc aatggagcgc ctgccggccc agtatcagcc cgtcatactt    4140
gaagctagac aggcttatct tggacaagaa gaagatcgct tggcctcgcg cgcagatcag    4200
ttggaagaat ttgtccacta cgtgaaaggc gagatcacca aggtagtcgg caaataatgt    4260
ctaacaattc gttcaagccg acgccgcttc gcggcgcggc ttaactcaag cgttagatgc   4320
actaagcaca taattgctca cagccaaact atcaggtcaa gtctgctttt attattttta   4380
agcgtgcata taagcccta cacaaattgg gagatatatc atgaaaggct ggcttttttct    4440 tgttatcgca atagttggcg aagtaatcgc aacatccgca ttaaaatcta gcgagggctt   4500
tactaagctg atccggtgga tgaccttttg aatgaccttt aatagattat attactaatt   4560
aattggggac cctagaggtc ccctttttta ttttaaaaat ttttttcacaa aacggtttac    4620 aagcataaag cttccgcggt acccgggaat tcgccctttc aagcttcaga tcaattcgcg    4680
ctaacttaca ttaattgcgt tgcgctcact gcccgctttc cagtcgggaa acctgtcgtg   4740
ccagctgcat taatgaatcg gccaacgcgc ggggagaggc ggtttgcgta ttgggcgcca    4800
gggtggtttt tcttttcacc agtgagacgg gcaacagctg attgcccttc accgcctggc   4860
cctgagagag ttgcagcaag cggtccacgc tggtttgccc cagcaggcga aaatcctgtt   4920
tgatggtggt taacggcggg atataacatg agctgtcttc ggtatcgtcg tatcccacta   4980
ccgagatatc cgcaccaacg cgcagcccgg actcggtaat ggcgcgcatt gcgcccagcg   5040
ccatctgatc gttggcaacc agcatcgcag tgggaacgat gccctcattc agcatttgca   5100
tggtttgttg aaaaccggac atggcactcc agtcgccttc ccgttccgct atcggctgaa   5160
tttgattgcg agtgagatat ttatgccagc cagccagacg cagacgcgcc gagacagaac   5220
ttaatgggcc cgctaacagc gcgatttgct ggtgacccaa tgcgaccaga tgctccacgc   5280
ccagtcgcgt accgtcttca tgggagaaaa taatactgtt gatgggtgtc tggtcagaga   5340
```

```
catcaagaaa taacgccgga acattagtgc aggcagcttc cacagcaatg gcatcctggt   5400
catccagcgg atagttaatg atcagcccac tgacgcgttg cgcgagaaga ttgtgcaccg   5460
ccgctttaca ggcttcgacg ccgcttcgtt ctaccatcga caccaccacg ctggcaccca   5520
gttgatcggc gcgagattta atcgccgcga caatttgcga cggcgcgtgc agggccagac   5580
tggaggtggc aacgccaatc agcaacgact gtttgcccgc cagttgttgt gccacgcggt   5640
tgggaatgta attcagctcc gccatcgccg cttccacttt ttcccgcgtt ttcgcagaaa   5700
cgtggctggc ctggttcacc acgcgggaaa cggtctgata agagacaccg gcatactctg   5760
cgacatcgta taacgttact ggtttcacat tcaccaccct gaattgactc tcttccgggc   5820
gctatcatgc cataccgcga aaggttttgc accattcgat ggtgtcaacg taaatgcatg   5880
ccgcttcgcc ttcgcgcaag cttagaaggg cgaattccgg acatatggat cttgggggaa   5940
attaagacca aactcgatga cctccaaaaa gatgtaactt ctcttaagat cgatatggca   6000
acggtgaaaa ccgagttatc tgcggtcagg atggagatag gtacagtcaa ggatgatgtt   6060
aaagatgtca aagggcgggc taatgctcaa atttgggcgt tgattcttgc cgtcatcgga   6120
gccataatta ccaccttggt gcgttttggc attttcccta atccctaaca aaaaagcgac   6180
caggcttttc tttcaattgc ccgatcgcct ttgatatttt cccaaaggat aaaagctagt   6240
ccattcagaa tcgagcctta aagtactccc atattggcta gccccagaat tactccagcg   6300
ccgaggatgt ggccaaagct agcggtgccc agcacagccc ctaaaccaaa gccgccaaag   6360
aagttagagg aaggcatggg ggtgcccaca ttttgttgtt tgatggtcaa tttaccaaag   6420
gcgatcgcca aaatgttgca agcaatcatc accccagcaa ctttagggct ccaggacagg   6480
gtggcgggaa cggcggtggc caacaaaaag ctatgcattg agattctcca gaataaagac   6540 ggttttttaaa gggatagccc cacgctaatg ggggtcttta aaaatctcat cttacgggga   6600
cgctctgccc ctgggaaacc accgttgcaa tacttaacaa attttcgttt ttagcttggc   6660
aaatgtcttt ggcaaaattg gttgatctgg cttaaatcgt cagttatttg ccctggaata   6720
gtctggggac gggcaattct gatcagattt acccccaacg cttccgccac tttttgctta   6780
accaattctc cccctgggc accggaggct ttagttacca cccccttgaat ttgccattgt   6840 tgccacaggg cttttttccaa tggttcggct acggggggggc gcaaagcaat gatacggtcg   6900
gaagtaaacc cagcggcgat cgcctgggct agggcttggg gatagggcag aatacgggca   6960
aatagggccc agcttggcgt aatcatggtc atagctgttt cctgtgtgaa attgttatcc   7020
gctcacaatt ccacacaaca tacgagccgg aagcataaag tgtaaagcct ggggtgccta   7080
atgagtgagc taactcacat taattgcgtt gcgctcactg cccgctttcc agtcgggaaa   7140
cctgtcgtgc cagctgcatt aatgaatcgg ccaacgcgcg gggagaggcg gtttgcgtat   7200
tgggcgctct tccgcttcct cgctcactga ctcgctgcgc tcggtcgttc ggctgcggcg   7260
agcggtatca gctcactcaa aggcggtaat acggttatcc acagaatcag gggataacgc   7320
aggaaagaac atgtgagcaa aaggccagca aaaggccagg aaccgtaaaa aggccgcgtt   7380
gctggcgttt ttccataggc tccgcccccc tgacgagcat cacaaaaatc gacgctcaag   7440
tcagaggtgg cgaaacccga caggactata aagataccag gcgtttcccc ctggaagctc   7500
cctcgtgcgc tctcctgttc cgaccctgcc gcttaccgga tacctgtccg cctttctccc   7560
ttcgggaagc gtggcgcttt ctcatagctc acgctgtagg tatctcagtt cggtgtaggt   7620
cgttcgctcc aagctgggct gtgtgcacga accccccgtt cagcccgacc gctgcgcctt   7680
```

```
atccggtaac tatcgtcttg agtccaaccc ggtaagacac gacttatcgc cactggcagc    7740
agccactggt aacaggatta gcagagcgag gtatgtaggc ggtgctacag agttcttgaa    7800
gtggtggcct aactacggct acactagaag gacagtattt ggtatctgcg ctctgctgaa    7860
gccagttacc ttcggaaaaa gagttggtag ctcttgatcc ggcaaacaaa ccaccgctgg    7920
tagcggtggt ttttttgttt gcaagcagca gattacgcgc agaaaaaaag gatctcaaga    7980
agatcctttg atcttttcta cggg                                          8004

<210> SEQ ID NO 2
<211> LENGTH: 9634
<212> TYPE: DNA
<213> ORGANISM: Artificial Sequence
<220> FEATURE:
<223> OTHER INFORMATION: pSGI-KF01 plasmid sequence

<400> SEQUENCE: 2
gtctgacgct cagtggaacg aaaactcacg ttaagggatt ttggtcatga gattatcaaa      60
aaggatcttc acctagatcc ttttaaatta aaaatgaagt tttaaatcaa tctaaagtat     120
atatgagtaa acttggtctg acagttacca atgcttaatc agtgaggcac ctatctcagc     180
gatctgtcta tttcgttcat ccatagttgc ctgactcccc gtcgtgtaga taactacgat     240
acgggagggc ttaccatctg gccccagtgc tgcaatgata ccgcgagacc cacgctcacc     300
ggctccagat ttatcagcaa taaaccagcc agccggaagg gccgagcgca gaagtggtcc     360
tgcaacttta tccgcctcca tccagtctat taattgttgc cgggaagcta gagtaagtag     420
ttcgccagtt aatagtttgc gcaacgttgt tgccattgct acaggcatcg tggtgtcacg     480
ctcgtcgttt ggtatggctt cattcagctc cggttcccaa cgatcaaggc gagttacatg     540
atcccccatg ttgtgcaaaa aagcggttag ctccttcggt cctccgatcg ttgtcagaag     600
taagttggcc gcagtgttat cactcatggt tatggcagca ctgcataatt ctcttactgt     660
catgccatcc gtaagatgct tttctgtgac tggtgagtac tcaaccaagt cattctgaga     720
atagtgtatg cggcgaccga gttgctcttg cccggcgtca atacgggata ataccgcgcc     780
acatagcaga actttaaaag tgctcatcat tggaaaacgt tcttcgggc gaaaactctc      840 aaggatctta ccgctgttga tccagttcga tgtaaccc actcgtgcac ccaactgatc      900
ttcagcatct tttactttca ccagcgtttc tgggtgagca aaaacaggaa ggcaaaatgc     960
cgcaaaaaag ggaataaggg cgacacggaa atgttgaata ctcatactct tcctttttca    1020
atattattga agcatttatc agggttattg tctcatgagc ggatacatat ttgaatgtat    1080
ttagaaaaat aaacaaatag gggttccgcg cacatttccc cgaaaagtgc cacctgacgt    1140
ctaagaaacc attattatca tgacattaac ctataaaaat aggcgtatca cgaggccctt    1200
tcgtctcgcg cgtttcggtg atgacggtga aaacctctga cacatgcagc tcccggagac    1260
ggtcacagct tgtctgtaag cggatgccgg gagcagacaa gcccgtcagg gcgcgtcagc    1320
gggtgttggc gggtgtcggg gctggcttaa ctatgcggca tcagagcaga ttgtactgag    1380
agtgcaccat aaaattgtaa acgttaatat tttgttaaaa ttcgcgttaa attttgtta     1440 aatcagctca ttttttaacc aataggccga atcggcaaa atcccttata aatcaaaaga    1500
atagcccgag atagggttga gtgttgttcc agtttggaac aagagtccac tattaaagaa    1560
cgtggactcc aacgtcaaag ggcgaaaaac cgtctatcag ggcgatggcc cactacgtga    1620
accatcaccc aaatcaagtt ttttggggtc gaggtgccgt aaagcactaa atcggaaccc    1680
taaagggagc ccccgattta gagcttgacg gggaaagccg gcgaacgtgg cgagaaagga    1740
```

```
agggaagaaa gcgaaaggag cgggcgctag ggcgctggca agtgtagcgg tcacgctgcg      1800
cgtaaccacc acacccgccg cgcttaatgc gccgctacag ggcgcgtact atggttgctt      1860
tgacgtatgc ggtgtgaaat accgcacaga tgcgtaagga gaaataccg catcaggcgc       1920 cattcgccat tcaggctgcg caactgttgg gaagggcgat cggtgcgggc ctcttcgcta      1980
ttacgccagc tggcgaaagg gggatgtgct gcaaggcgat taagttgggt aacgccaggg      2040
ttttcccagt cacgacgttg taaaacgacg gccagtgcca agctattgct gaagcggaat      2100
ccctggttaa tgccgccgcc gatgccaatt gcattctcca agtggggcac attgaacgct      2160
tcaacccggc attttttagag ctaaccaaaa ttctcaaaac ggaagagtta ttggcgatcg     2220
aagcccatcg catgagtccc tattcccagc gggccaatga tgtctccgtg gtattggatt     2280
tgatgatcca tgacattgac ctgttgctgg aattggtggg ttcggaagtg gttaaactgt     2340
ccgccagtgg cagtcgggct tctgggtcag atatttggga ttatgtcacc gctacgttag     2400
gcttctcctc cggcattgtg gccacccctca ccgccagtaa ggtcacccat cgtaaaattc     2460
gttccatcgc cgcccactgc aaaaattccc tcaccgaagc ggattttctc aataacgaaa     2520
ttttgatcca tcgccaaacc accgctgatt ggagcgcgga ctatgccag gtattgtatc      2580 gccaggatgg tctaatcgaa aaggtttaca ccagtaatat tgaacctctc cacgctgaat     2640
tagaacattt tattcattgt gttaggggag gtgatcaacc ctcagtgggg ggagaacagg     2700
ccctcaaggc cctgaagtta gccagtttaa ttgaagaaat ggccctggac agtcaggaat     2760
ggcatggggg ggaagttgtg acagaatatc aagatgccac cctggccctc agtgcgagtg     2820
tttaaatcaa cttaattaat gcaattattg cgagttcaaa ctcgataact ttgtgaaata     2880
ttactgttga attaatctat gactattcaa tacacccccc tagccgatcg cctgttggcc     2940
tacctcgccg ccgatcgcct aaatctcagc gccaagagta gttccctcaa caccagtatt     3000
ctgctcagca gtgacctatt caatcaggaa gggggaattg taacagccaa ctatggcttt     3060
gatggttata tggtaccata tgcatgcgag ctcactatta actggcggga ttaccattac     3120
tggttttacc ggtactaatg gcaccaatat tccgggcatt cttttggacg cactcagtgc     3180
ggcccttaac gatgtcagta ccgtcctcca agcgcagtaa atgctggtag tgggagcgac     3240
caccttcatt agaaggatcc atcgcggtca cagattccag cacgctatcg cgaccgcact     3300
cgcgacgata ctccagagtt aagaaacaca gttcatgagt ttccaagacc tcggtcggca     3360
tgctctctaa gatccagccg atatacttaa cgttgttaac gtgctgatta acatctaagt     3420
cattccaacg cggagtcaaa cctttacgga tgctgtcgcc ggttttcaca tcgaacttgt     3480
gtaacttacg gtcgccgtcc tcgatcacgg gagggctgtc gacgaagtgc ggagcaatct     3540
cttggctgac ttcgtaaggc agtttagaca gacgacgggc cttttggttc atcatcgccc     3600
atgcagacgt cgcgcggatc aggatttcgc cggtattaca gtcggaaatc agccaatcac     3660
gacccatacc attcttgccg ctttgggaaa cccaagtgtt aatctcaacg gtatcacccc     3720
aggtagggta gcggttgacc atgatgtgca tgcgggtaac cacccagatc aagtcacgtt     3780
tgcacatctc gggggtgcga ccaaaaccct cattcaacaa gcgaatggat ttgcaatgat     3840
tcaagctagt ttcctgcaga tggttcatta aggtttcaat ggatgcacga cgatctgcac     3900
cgatttcata agaacgaatg ctaaaagatt gacgaaacac taagccatcc tgcacaatgc     3960
gttccatgcc aaaagaatcc actaacatat cggagcgctt gctcttgcgg tctaacatag     4020
tccactgttt ctctgcggca acaaagacag tggtaatcgc cgtcaataac atggaccagt     4080
```

-continued

| | |
|---|---|
| cgggtaattg gttgatgaac gcgcgtggcg gtggggaaga agaagtgtcc tcttgcgtat | 4140 |
| tcaaggagcc gctcttcaga gagacagcgc taccgttcgc catggttttt ttcctcctta | 4200 |
| gtgtgaaatt gttatccgct cacaattcca cacattatac gagccggatg attaattgtc | 4260 |
| aacagctcat ttcagcctca ggactagtgg atctaccagg ttgtccttgg cgcagcgctt | 4320 |
| cccacgctga gagggtgtag cccgtcacgg gtaaccgata tcgtcgacag gcctctagac | 4380 |
| ccgggctcga gctagcaagc ttggccggat ccggccggat ccggagtttg tagaaacgca | 4440 |
| aaaaggccat ccgtcaggat ggccttctgc ttaatttgat gcctggcagt ttatggcggg | 4500 |
| cgtcctgccc gccacccctcc gggccgttgc ttcgcaacgt tcaaatccgc tcccggcgga | 4560 |
| tttgtcctac tcaggagagc gttcaccgac aaacaacaga taaaacgaaa ggcccagtct | 4620 |
| ttcgactgag cctttcgttt tatttgatgc ctggcagttc cctactctcg catggggaga | 4680 |
| ccccacacta ccatcggcgc tacggcgttt cacttctgag ttcggcatgg ggtcaggtgg | 4740 |
| gaccaccgcg ctactgccgc caggcaaatt ctgttttatt gagccgttac cccacctact | 4800 |
| agctaatccc atctgggcac atccgatggc aagaggcccg aaggtccccc tctttggtct | 4860 |
| tgcgacgtta tgcggtatta gctaccgttt ccagtagtta tccccctcca tcaggcagtt | 4920 |
| tcccagacat tactcacccg tccgccactc gtcagcaaag aagcaagctt agatcgacct | 4980 |
| gcagggggggg ggggaaagc cacgttgtgt ctcaaaatct ctgatgttac attgcacaag | 5040 |
| ataaaaatat atcatcatga acaataaaac tgtctgctta cataaacagt aatacaaggg | 5100 |
| gtgttatgag ccatattcaa cgggaaacgt cttgctcgag gccgcgatta aattccaaca | 5160 |
| tggatgctga tttatatggg tataaatggg ctcgcgataa tgtcgggcaa tcaggtgcga | 5220 |
| caatctatcg attgtatggg aagcccgatg cgccagagtt gtttctgaaa catggcaaag | 5280 |
| gtagcgttgc caatgatgtt acagatgaga tggtcagact aaactggctg acggaattta | 5340 |
| tgcctcttcc gaccatcaag cattttatcc gtactcctga tgatgcatgg ttactcacca | 5400 |
| ctgcgatccc cgggaaaaca gcattccagg tattagaaga atatcctgat tcaggtgaaa | 5460 |
| atattgttga tgcgctggca gtgttcctgc gccggttgca ttcgattcct gtttgtaatt | 5520 |
| gtccttttaa cagcgatcgc gtatttcgtc tcgctcaggc gcaatcacga atgaataacg | 5580 |
| gtttggttga tgcgagtgat tttgatgacg agcgtaatgg ctggcctgtt gaacaagtct | 5640 |
| ggaaagaaat gcataagctt ttgccattct caccggattc agtcgtcact catggtgatt | 5700 |
| tctcacttga taaccttatt tttgacgagg ggaaattaat aggttgtatt gatgttggac | 5760 |
| gagtcggaat cgcagaccga taccaggatc ttgccatcct atggaactgc ctcggtgagt | 5820 |
| tttctccttc attacagaaa cggctttttc aaaaatatgg tattgataat cctgatatga | 5880 |
| ataaattgca gtttcatttg atgctcgatg agttttttcta atcagaattg gttaattggt | 5940 |
| tgtaacactg gcagagcatt acgctgactt gacgggacgg cggctttgtt gaataaatcg | 6000 |
| aacttttgct gagttgaagg atcagatcac gcatcttccc gacaacgcag accgttccgt | 6060 |
| ggcaaagcaa aagttcaaaa tcaccaactg gtccacctac aacaaagctc tcatcaaccg | 6120 |
| tggctccctc actttctggc tggatgatgg ggcgattcag gctggtatg agtcagcaac | 6180 |
| accttcttca cgaggcagac ctcagcgccc cccccccct gcaggtcgat ctggtaaccc | 6240 |
| cagcgcggtt gctaccaagt agtgacccgc ttcgtgatgc aaaatccgct gacgatattc | 6300 |
| gggcgatcgc tgctgaatgc catcgagcag taacgtggcg aattcgccct ttcaagcttc | 6360 |
| agatcaattc gcgctaactc acattaattg cgttgcgctc actgcccgct ttccagtcgg | 6420 |
| gaaacctgtc gtgccagctg cattaatgaa tcggccaacg cgcggggaga ggcggtttgc | 6480 |

```
gtattgggcg ccagggtggt ttttcttttc accagtgaga cgggcaacag ctgattgccc    6540
ttcaccgcct ggccctgaga gagttgcagc aagcggtcca cgctggtttg ccccagcagg    6600
cgaaaatcct gtttgatggt ggttgacggc gggataaac atgagctgtc ttcggtatcg     6660
tcgtatccca ctaccgagat atccgcacca acgcgcagcc cggactcggt aatggcgcgc    6720
attgcgccca gcgccatctg atcgttggca accagcatcg cagtgggaac gatgccctca    6780
ttcagcattt gcatggtttg ttgaaaaccg gacatggcac tccagtcgcc ttcccgttcc    6840
gctatcggct gaatttgatt gcgagtgaga tatttatgcc agccagccag acgcagacgc    6900
gccgagacag aacttaatgg gcccgctaac agcgcgattt gctggtgacc caatgcgacc    6960
agatgctcca cgcccagtcg cgtaccgtct tcatgggaga aaataatact gttgatgggt    7020
gtctggtcag agacatcaag aaataacgcc ggaacattag tgcaggcagc ttccacagca    7080
atggcatcct ggtcatccag cggatagtta atgatcagcc cactgacgcg ttgcgcgaga    7140
agattgtgca ccgccgcttt acaggcttcg acgccgcttc gttctaccat cgacaccacc    7200
acgctggcac ccagttgatc ggcgcgagat ttaatcgccg cgacaatttg cgacggcgcg    7260
tgcagggcca gactggaggt ggcaacgcca atcagcaacg actgtttgcc cgccagttgt    7320
tgtgccacgc ggttgggaat gtaattcagc tccgccatcg ccgcttccac ttttttcccgc   7380 gttttcgcag aaacgtggct ggcctggttc accacgcggg aaacggtctg ataagagaca    7440
ccggcatact ctgcgacatc gtataacgtt actggtttca cattcaccac cctgaattga    7500
ctctcttccg ggcgctatca tgccataccg cgaaaggttt tgcaccattc gatggtgtca    7560
acgtaaatgc atgccgcttc gccttcgcgc aagcttagaa gggcgaattc ggtaccggta    7620 tggatgcac cgatgcggaa tcccaacaga ttgcctttga caacaatgtg gcctggaata    7680
acctggggga tttgtccacc accacccaac gggcctacac ttcggctatt agcacagaca    7740
cagtgcagag tgtttatggc gttaatctgg aaaaaaacga taacattccc attgtttttg    7800
cgtggcccat ttttcccacc acccttaatc ccacagattt tcaggtaatg cttaacacgg    7860
gggaaattgt caccccggtg atcgcctctt tgattcccaa cagtgaatac aacgaacggc    7920
aaacggtagt aattacgggc aattttggta atcgtttaac cccaggcacg gagggagcga    7980
tttatcccgt ttccgtaggc acagtgttgg acagtactcc tttggaaatg gtgggaccca    8040
acggcccggt cagtgcggtg ggtattacca ttgatagtct caaccctac gtggccggca     8100 atggtcccaa aattgtcgcc gctaagttag accgcttcag tgacctgggg gaagggctc     8160 ccctctggtt agccaccaat caaaataaca gtggcgggga tttatatgga gaccaagccc    8220
aatttcgttt gcgaatttac accagcgccg gttttttcccc cgatggcatt gccagtttac    8280
tacccacaga atttgaacgg tattttcaac tccaagcgga agatattacg ggacggacag    8340
ttatcctaac ccaaactggt gttgattatg aaattcccgg ctttggtctg gtgcaggtgt    8400
tggggctggc ggatttggcc ggggttcagg acagctatga cctgacttac atcgaagatc    8460
atgacaacta ttacgacatt atcctcaaag gggacgaagc cgcagttcgc caaattaaga    8520
gggttgcttt gccctccgaa ggggattatt cggcggttta taatcccggt ggccccggca    8580
atgatccaga gaatggtccc ccaaattcgt aatcatggtc atagctgttt cctgtgtgaa    8640
attgttatcc gctcacaatt ccacacaaca tacgagccgg aagcataaag tgtaaagcct    8700
ggggtgccta atgagtgagc taactcacat taattgcgtt gcgctcactg cccgctttcc    8760
agtcgggaaa cctgtcgtgc cagctgcatt aatgaatcgg ccaacgcgcg gggagaggcg    8820
```

| | |
|---|---|
| gtttgcgtat tgggcgctct tccgcttcct cgctcactga ctcgctgcgc tcggtcgttc | 8880 |
| ggctgcggcg agcggtatca gctcactcaa aggcggtaat acggttatcc acagaatcag | 8940 |
| gggataacgc aggaaagaac atgtgagcaa aaggccagca aaaggccagg aaccgtaaaa | 9000 |
| aggccgcgtt gctggcgttt ttccataggc tccgccccc tgacgagcat cacaaaaatc | 9060 |
| gacgctcaag tcagaggtgg cgaaacccga caggactata aagataccag gcgtttcccc | 9120 |
| ctggaagctc cctcgtgcgc tctcctgttc cgaccctgcc gcttaccgga tacctgtccg | 9180 |
| cctttctccc ttcgggaagc gtggcgcttt ctcatagctc acgctgtagg tatctcagtt | 9240 |
| cggtgtaggt cgttcgctcc aagctgggct gtgtgcacga accccccgtt cagcccgacc | 9300 |
| gctgcgcctt atccggtaac tatcgtcttg agtccaaccc ggtaagacac gacttatcgc | 9360 |
| cactggcagc agccactggt aacaggatta gcagagcgag gtatgtaggc ggtgctacag | 9420 |
| agttcttgaa gtggtggcct aactacggct acactagaag gacagtattt ggtatctgcg | 9480 |
| ctctgctgaa gccagttacc ttcggaaaaa gagttggtag ctcttgatcc ggcaaacaaa | 9540 |
| ccaccgctgg tagcggtggt ttttttgttt gcaagcagca gattacgcgc agaaaaaaag | 9600 |
| gatctcaaga agatcctttg atctttcta cggg | 9634 |

<210> SEQ ID NO 3
<211> LENGTH: 8594
<212> TYPE: DNA
<213> ORGANISM: Artificial Sequence
<220> FEATURE:
<223> OTHER INFORMATION: pSGI-TW03 complete genome sequence

<400> SEQUENCE: 3

| | |
|---|---|
| gttctttcct gcgttatccc ctgattctgt ggataaccgt attaccgcct ttgagtgagc | 60 |
| tgataccgct cgccgcagcc gaacgaccga gcgcagcgag tcagtgagcg aggaagcgga | 120 |
| agagcgccca atacgcaaac cgcctctccc cgcgcgttgg ccgattcatt aatgcagctg | 180 |
| gcacgacagg tttcccgact ggaaagcggg cagtgagcgc aacgcaatta atgtgagtta | 240 |
| gctcactcat taggcacccc aggctttaca ctttatgctt ccggctcgta tgttgtgtgg | 300 |
| aattgtgagc ggataacaat ttcacacagg aaacagctat gaccatgatt acgccaagct | 360 |
| tggtaccgag ctcggatcca ctagtaacgg ccgccagtgt gctggaattc gcccttctcg | 420 |
| agccccgtg ctatgactag cggcgatcgc ataccggcc acgaccattt gcattggatc | 480 |
| cccaacggcg gccacaactt ccatggcatt gagatgcggg gaatgatgtt ctagactctg | 540 |
| acgcaccaaa gccaattttt gttgatggtt gcaatgggga tgactactgt tcactttgcc | 600 |
| cccagcgtca atgcctagac ctagcagtac ccccagggct gtggtagtgc cccccaccac | 660 |
| gcattcgctt agcactaagt aactttcggc atgttcctgg gctaactgtg cgccccactg | 720 |
| caaaccctgc tgaaaagat gctccaccag gccaacggt aacgcttgcc ctgtggaaag | 780 |
| acagcgggcg ggttgtccgt ctagattgat gactggcacc gctgggggaa tgggtaaacc | 840 |
| agagttaaat aaataaaccg gagtatgag gcatccacc aacgctttgg tgatgaacac | 900 |
| tggggaaacc ccagaaatga ggggaggtaa gggataggtt gccctgccg tagttccctt | 960 |
| gattaaaaat tccgcatcgg cgatcgccgt caattttcga tcagcggggg ttttacccgc | 1020 |
| cgcagaaatg cccggaatta accagtttc cgtaaagccc aacacacaga caaacaccgg | 1080 |
| tggacagtgg ccatggcgct caatccagga taaagcttgg tcagactggg tataaactgt | 1140 |
| caacatattt ctgcaagagt gggcccaatt gggaaaatca acctcaaatc cattggaata | 1200 |
| gccttttttc aaccgtaaaa atccaacttt ctctcttccc ttcttccttc catctgatta | 1260 |

```
tggttacgcc aattaactac cattccatcc attgcctggc ggatatctgg gctatcaccg    1320
gagaaaattt tgccgatatt gtggccctca acgatcgcca tagtcatccc cccgtaactt    1380
taacctatgc ccaattggtc acacgggata ataccgcgcc acatagcaga actttaaaag    1440
tgctcatcat tggaaaacgt tcttcggggc gaaaactctc aaggatctta ccgctgttga    1500
gatccagttc gatgtaaccc actcgtgcac ccaactgatc ttcagcatct tttactttca    1560
ccagcgtttc tgggtgagca aaaacaggaa ggcaaaatgc cgcaaaaaag ggaataaggg    1620
cgacacggaa atgttgaata ctcatactct tcctttttca atattattga agcatttatc    1680
agggttattg tctcatgagc ggatacatat ttgaatgtat ttagaaaaat aaacaaatag    1740
gggttccgcg cacatttccc cgaaaagtgc cacctgacgt ctaagaaacc attattatca    1800
tgacattaac ctataaaaat aggcgtatca cgaggccctt tcgtcttcga taaatacct    1860 gtgacggaag atcacttcgc agaataaata atcctggtg tccctgttga taccgggaag    1920
ccctgggcca acttttggcg aaaatgagac gttgatcggc acgtaagagg ttccaacttt    1980
caccataatg aaataagatc actaccgggc gtattttttg agttatcgag attttcagga    2040
gctaaggaag ctaaaatgga gaaaaaaatc actggatata ccaccgttga tatatcccaa    2100
tggcatcgta agaacatttt tgaggcattt cagtcagttg ctcaatgtac ctataaccag    2160
accgttcagc tggatattac ggccttttta aagaccgtaa agaaaaataa gcacaagttt    2220
tatccggcct ttattcacat tcttgcccgc ctgatgaatg ctcatccgga attccgtatg    2280
gcaatgaaag acggtgagct ggtgatatgg gatagtgttc accctgttta caccgttttc    2340
catgagcaaa ctgaaacgtt ttcatcgctc tggagtgaat accacgacga tttccggcag    2400
tttctacaca tatattcgca agatgtggcg tgttacggtg aaaacctggc ctatttccct    2460
aaagggttta ttgagaatat gttttttcgtc tcagccaatc cctgggtgag tttcaccagt    2520
tttgatttaa acgtggccaa tatggacaac ttcttcgccc ccgttttcac catgggcaaa    2580
tattatacgc aaggcgacaa ggtgctgatg ccgctggcga ttcaggttca tcatgccgtt    2640
tgtgatggct tccatgtcgg cagaatgctt aatgaattac aacagtactg cgatgagtgg    2700
cagggcgggg cgtaattttt ttaaggcagt tattggtgcc cttaaacgcc tggttgctac    2760
gcctgaataa gtgataataa gcggatgaat ggcagaaatt cgaaagcaaa ttcgacccgg    2820
tcgtcggttc agggcagggt cgttaaatag ccgcttatgt ctattgctgg tttaccggtt    2880
tattgactac cggaagcagt gtgaccgtgt gcttctcaaa tgcctgaggt atactgaaat    2940
gagctgttga caattaatca tccggctcgt ataatgtgtg gaattgtgag cggataacaa    3000
tttcacacta aggaggaaaa aaaccatggc gaacggtagc gctgtctctc tgaagagcgg    3060
ctccttgaat acgcaagagg acacttcttc ttccccaccg ccacgcgcgt tcatcaacca    3120
attacccgac tggtccatgt tattgacggc gattaccact gtctttgttg ccgcagagaa    3180
acagtggact atgttagacc gcaagagcaa gcgctccgat atgttagtgg attcttttgg    3240
catggaacgc attgtgcagg atggcttagt gttccgtcaa tcttttagca ttcgttctta    3300
tgaaatcggt gcagatcgtc gtgcatccat tgaaaaccta atgaaccatc tgcaggaaac    3360
tagcttgaat cattgcaaat ccattcgctt gttgaatgag ggttttggtc gcaccccga    3420 gatgtgcaaa cgtgacttga tctgggtggt tacccgcatg cacatcatgg tcaaccgcta    3480
ccctacctgg ggtgataccg ttgagattaa cacttgggtt tcccaaagcg gcaagaatgg    3540
tatgggtcgt gattggctga tttccgactg taataccggc gaaatcctga tccgcgcgac    3600
```

```
gtctgcatgg gcgatgatga accaaaagac ccgtcgtctg tctaaactgc cttacgaagt    3660
cagccaagag attgctccgc acttcgtcga cagccctccc gtgatcgagg acggcgaccg    3720
taagttacac aagttcgatg tgaaaaccgg cgacagcatc cgtaaaggtt tgactccgcg    3780
ttggaatgac ttagatgtta atcagcacgt taacaacgtt aagtatatcg ctggatctt     3840 agagagcatg ccgaccgagg tcttggaaac tcatgaactg tgtttcttaa ctctggagta    3900
tcgtcgcgag tgcggtcgcg atagcgtgct ggaatctgtg accgcgatgg atccttctaa    3960
tgaaggtggt cgctcccact accagcattt actgcgcttg gaggacggta ctgacatcgt    4020
taagggccgc actgagtggc gtccaaagaa tgcccggaat attggtgcca ttagtaccgg    4080
taaaaccagt aatggtaatc cgccagtta atctagatat ctgcaggcct aagctttatg     4140
cttgtaaacc gttttgtgaa aaatttta aataaaaaa ggggacctct agggtcccca       4200
attaattagt aatataatct attaaaggtc attcaaaagg tcatccaccg gatcaattcc    4260
cctgctcgcg caggctgggt gccaggcccg atcctgaggc cagtttgctc aggctctccc    4320
cgtggaggta ataattgacg atatgatcga ccaattgcgg gaagaaatta cagcttttgc    4380
cgctggccta cagagtttag gagttacccc catcaacacc tggccatttt cgccgacaac    4440 agccccggt ggtttatcgc cgatcaaggc agtatgttgg ctggagccgt caacgccgtc     4500
cgttctgccc aagcagagcg ccaggaatta ctctacatcc tagaagacag caacagccgt    4560
actttaatcg cagaaaatcg gcaaacccta agcaaattgg ccctagatgg cgaaaccatt    4620
gacctgaaac taatcatcct cctcaccgat gaagaagtgg cagaggacag cgccattccc    4680
caatataact ttgcccaggt catggcccta ggggccggca aaatccccac tcccgttccc    4740
cgccaggaag aagatttagc caccctgatc tacacctccg gcaccacagg acaacccaaa    4800
ggggtgatgc tcagccacgg taatttattg caccaagtac gggaattgga ttcggtgatt    4860
attccccgcc ccggcgatca ggtgttgagc attttgccct gttggcactc cctagaaaga    4920
agcgccgaat attttcttct ttcccggggc tgcacgatga actacaccag cattcgccat    4980
ttcaaggggg atgtgaagga cattaaaccc catcacattg tcggtgtgcc ccggctgtgg    5040
gaatccctct acgaaggggt acaaaaaacg ttccgggcta agggcgaatt ctgcagatat    5100
ccatcacact ggcggccgct cgagcatgca tctagagggc ccaattcgcc ctatagtgag    5160
tcgtattaca attcactggc cgtcgtttta caacgtcgtg actgggaaaa ccctggcgtt    5220
acccaactta atcgccttgc agcacatccc cctttcgcca gctggcgtaa tagcgaagag    5280
gcccgcaccg atcgcccttc ccaacagttg cgcagcctga atggcgaatg gacgcgccct    5340
gtagcggcgc attaagcgcg gcgggtgtgg tggttacgcg cagcgtgacc gctacacttg    5400
ccagcgccct agcgcccgct cctttcgctt tcttcccttc ctttctcgcc acgttcgccg    5460
gctttccccg tcaagctcta aatcgggggc tccctttagg gttccgattt agtgctttac    5520
ggcacctcga ccccaaaaaa cttgattagg gtgatggttc acgtagtggg ccatcgccct    5580
gatagacggt ttttcgccct ttgacgttgg agtccacgtt ctttaatagt ggactcttgt    5640
tccaaactgg aacaacactc aaccctatct cggtctattc ttttgattta agggattt      5700 tgccgatttc ggcctattgg ttaaaaaatg agctgattta caaaaatttt aacgcgaatt    5760
ttaacaaaat tcagggcgca agggctgcta aggaagcgg aacacgtaga aagccagtcc     5820
gcagaaacgg tgctgacccc ggatgaatgt cagctactgg gctatctgga caagggaaaa    5880
cgcaagcgca aagagaaagc aggtagcttg cagtgggctt acatggcgat agctagactg    5940
ggcggtttta tggacagcaa gcgaaccgga attgccagct ggggcgccct ctggtaaggt    6000
```

```
tgggaagccc tgcaaagtaa actggatggc tttcttgccg ccaaggatct gatggcgcag    6060
gggatcaaga tctgatcaag agacaggatg aggatcgttt cgcatgattg aacaagatgg    6120
attgcacgca ggttctccgg ccgcttgggt ggagaggcta ttcggctatg actgggcaca    6180
acagacaatc ggctgctctg atgccgccgt gttccggctg tcagcgcagg ggcgcccggt    6240 tcttttttgtc aagaccgacc tgtccggtgc cctgaatgaa ctgcaggacg aggcagcgcg    6300
gctatcgtgg ctggccacga cgggcgttcc ttgcgcagct gtgctcgacg ttgtcactga    6360
agcgggaagg gactggctgc tattgggcga agtgccgggg caggatctcc tgtcatccca    6420
ccttgctcct gccgagaaag tatccatcat ggctgatgca atgcggcggc tgcatacgct    6480
tgatccggct acctgcccat tcgaccacca agcgaaacat cgcatcgagc gagcacgtac    6540
tcggatggaa gccggtcttg tcgatcagga tgatctggac gaagagcatc aggggctcgc    6600
gccagccgaa ctgttcgcca ggctcaaggc gcgcatgccc gacggcgagg atctcgtcgt    6660
gacccatggc gatgcctgct tgccgaatat catggtggaa aatggccgct tttctggatt    6720
catcgactgt ggccggctgg gtgtggcgga ccgctatcag acatagcgt tggctacccg    6780 tgatattgct gaagagcttg gcggcgaatg ggctgaccgc ttcctcgtgc tttacggtat    6840
cgccgctccc gattcgcagc gcatcgcctt ctatcgcctt cttgacgagt tcttctgaat    6900 tgaaaagga gagtatgag tattcaacat tccgtgtcg cccttattcc ctttttgcg    6960 gcattttgcc ttcctgtttt tgctcaccca gaaacgctgg tgaaagtaaa agatgctgaa    7020
gatcagttgg gtgcacgagt gggttacatc gaactggatc tcaacagcgg taagatcctt    7080
gagagttttc gccccgaaga acgttttcca atgatgagca cttttaaagt tctgctatgt    7140
ggcgcggtat tatcccgtat tgacgccggg caagagcaac tcggtcgccg catacactat    7200
tctcagaatg acttggttga gtactcacca gtcacagaaa agcatcttac ggatggcatg    7260
acagtaagag aattatgcag tgctgccata accatgagtg ataacactgc ggccaactta    7320
cttctgacaa cgatcggagg accgaaggag ctaaccgctt ttttgcacaa catgggggat    7380
catgtaactc gccttgatcg ttgggaaccg gagctgaatg aagccatacc aaacgacgag    7440
cgtgacacca cgatgcctgt agcaatggca acaacgttgc gcaaactatt aactggcgaa    7500
ctacttactc tagcttcccg gcaacaatta atagactgga tggaggcgga taaagttgca    7560
ggaccacttc tgcgctcggc ccttccggct ggctggttta ttgctgataa atctggagcc    7620
ggtgagcgtg ggtctcgcgg tatcattgca gcactggggc cagatggtaa gccctcccgt    7680
atcgtagtta tctacacgac ggggagtcag gcaactatgg atgaacgaaa tagacagatc    7740
gctgagatag gtgcctcact gattaagcat tggtaactgt cagaccaagt ttactcatat    7800
atactttaga ttgatttaaa acttcatttt taatttaaaa ggatctaggt gaagatcctt    7860
tttgataatc tcatgaccaa aatcccttaa cgtgagtttt cgttccactg agcgtcagac    7920
cccgtagaaa agatcaaagg atcttcttga tccttttttt ttctgcgcgt aatctgctgc    7980
ttgcaaacaa aaaaaccacc gctaccagcg gtggtttgtt tgccggatca agagctacca    8040 actcttttc cgaaggtaac tggcttcagc agagcgcaga taccaaatac tgttcttcta    8100
gtgtagccgt agttaggcca ccacttcaag aactctgtag caccgcctac atacctcgct    8160
ctgctaatcc tgttaccagt ggctgctgcc agtggcgata agtcgtgtct taccgggttg    8220
gactcaagac gatagttacc ggataaggcg cagcggtcgg gctgaacggg gggttcgtgc    8280
acacagccca gcttggagcg aacgacctac accgaactga gatacctaca gcgtgagcta    8340
```

```
tgagaaagcg ccacgcttcc cgaagggaga aggcggaca ggtatccggt aagcggcagg    8400
gtcggaacag gagagcgcac gagggagctt ccagggggaa acgcctggta tctttatagt    8460
cctgtcgggt ttcgccacct ctgacttgag cgtcgatttt tgtgatgctc gtcagggggg    8520
cggagcctat ggaaaaacgc cagcaacgcg gccttttt ac ggttcctggc cttttgctgg    8580 cctttt gctc acat                                                    8594
```

<210> SEQ ID NO 4
<211> LENGTH: 1112
<212> TYPE: DNA
<213> ORGANISM: Artificial Sequence
<220> FEATURE:
<223> OTHER INFORMATION: Codon optimized nucleotide sequence of Cc1FatB1
   thioesterase gene, N-terminally truncated

<400> SEQUENCE: 4

```
atggcgaacg gtagcgctgt ctctctgaag agcggctcct tgaatacgca agaggacact      60
tcttcttccc caccgccacg cgcgttcatc aaccaattac ccgactggtc catgttattg     120
acggcgatta ccactgtctt tgttgccgca gagaaacagt ggactatgtt agaccgcaag     180
agcaagcgct ccgatatgtt agtggattct tttggcatgg aacgcattgt gcaggatggc     240
ttagtgtttc gtcaatcttt tagcattcgt tcttatgaaa tcggtgcaga tcgtcgtgca     300
tccattgaaa cctaatgaa ccatctgcag gaaactagct tgaatcattg caaatccatt     360
cgcttgttga atgagggttt tggtcgcacc cccgagatgt gcaaacgtga cttgatctgg     420
gtggttaccc gcatgcacat catggtcaac cgctacccta cctggggtga taccgttgag     480
attaacactt gggtttccca aagcggcaag aatggtatgg tcgtgattg gctgatttcc     540 gactgtaata ccggcgaaat cctgatccgc gcgacgtctg catgggcgat gatgaaccaa     600
aagacccgtc gtctgtctaa actgccttac gaagtcagcc aagagattgc tccgcacttc     660
gtcgacagcc ctcccgtgat cgaggacggc gaccgtaagt acacaagtt cgatgtgaaa     720 accggcgaca gcatccgtaa aggtttgact ccgcgttgga atgacttaga tgttaatcag     780
cacgttaaca cgttaagta tatcggctgg atcttagaga gcatgccgac cgaggtcttg     840
gaaactcatg aactgtgttt cttaactctg gagtatcgtc gcgagtgcgg tcgcgatagc     900
gtgctggaat ctgtgaccgc gatggatcct tctaatgaag gtggtcgctc ccactaccag     960
catttactgc gcttggagga cggtactgac atcgttaagg ccgcactga gtggcgtcca    1020 aagaatgccc ggaatattgg tgccattagt accggtaaaa ccagtaatgg taatcccgcc    1080
agttaataat gatcagatcc ggagtttgta ga                                 1112
```

<210> SEQ ID NO 5
<211> LENGTH: 361
<212> TYPE: PRT
<213> ORGANISM: Cuphea carthagenensis

<400> SEQUENCE: 5

```
Met Ala Asn Gly Ser Ala Val Ser Leu Lys Ser Gly Ser Leu Asn Thr
1               5                   10                  15

Gln Glu Asp Thr Ser Ser Ser Pro Pro Arg Ala Phe Ile Asn Gln
            20                  25                  30

Leu Pro Asp Trp Ser Met Leu Leu Thr Ala Ile Thr Thr Val Phe Val
        35                  40                  45

Ala Ala Glu Lys Gln Trp Thr Met Leu Asp Arg Lys Ser Lys Arg Ser
    50                  55                  60
```

Asp Met Leu Val Asp Ser Phe Gly Met Glu Arg Ile Val Gln Asp Gly
65                  70                  75                  80

Leu Val Phe Arg Gln Ser Phe Ser Ile Arg Ser Tyr Glu Ile Gly Ala
                85                  90                  95

Asp Arg Arg Ala Ser Ile Glu Thr Leu Met Asn His Leu Gln Glu Thr
            100                 105                 110

Ser Leu Asn His Cys Lys Ser Ile Arg Leu Leu Asn Glu Gly Phe Gly
        115                 120                 125

Arg Thr Pro Glu Met Cys Lys Arg Asp Leu Ile Trp Val Val Thr Arg
    130                 135                 140

Met His Ile Met Val Asn Arg Tyr Pro Thr Trp Gly Asp Thr Val Glu
145                 150                 155                 160

Ile Asn Thr Trp Val Ser Gln Ser Gly Lys Asn Gly Met Gly Arg Asp
                165                 170                 175

Trp Leu Ile Ser Asp Cys Asn Thr Gly Glu Ile Leu Ile Arg Ala Thr
            180                 185                 190

Ser Ala Trp Ala Met Met Asn Gln Lys Thr Arg Arg Leu Ser Lys Leu
        195                 200                 205

Pro Tyr Glu Val Ser Gln Glu Ile Ala Pro His Phe Val Asp Ser Pro
    210                 215                 220

Pro Val Ile Glu Asp Gly Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255

Asp Val Asn Gln His Val Asn Val Lys Tyr Ile Gly Trp Ile Leu
            260                 265                 270

Glu Ser Met Pro Thr Glu Val Leu Glu Thr His Glu Leu Cys Phe Leu
        275                 280                 285

Thr Leu Glu Tyr Arg Arg Glu Cys Gly Arg Asp Ser Val Leu Glu Ser
    290                 295                 300

Val Thr Ala Met Asp Pro Ser Asn Glu Gly Gly Arg Ser His Tyr Gln
305                 310                 315                 320

His Leu Leu Arg Leu Glu Asp Gly Thr Asp Ile Val Lys Gly Arg Thr
                325                 330                 335

Glu Trp Arg Pro Lys Asn Ala Arg Asn Ile Gly Ala Ile Ser Thr Gly
            340                 345                 350

Lys Thr Ser Asn Gly Asn Pro Ala Ser
        355                 360

<210> SEQ ID NO 6
<211> LENGTH: 41
<212> TYPE: DNA
<213> ORGANISM: Artificial Sequence
<220> FEATURE:
<223> OTHER INFORMATION: Primer YC-244

<400> SEQUENCE: 6
cactaaggag gaaaaaaacc atggcgaacg gtagcgctgt c                          41

<210> SEQ ID NO 7
<211> LENGTH: 50
<212> TYPE: DNA
<213> ORGANISM: Artificial Sequence
<220> FEATURE:
<223> OTHER INFORMATION: Primer YC-248

<400> SEQUENCE: 7
taccatatgc atgcgagctc actattaact ggcgggatta ccattactgg    50

<210> SEQ ID NO 8
<211> LENGTH: 21
<212> TYPE: DNA
<213> ORGANISM: Artificial Sequence
<220> FEATURE:
<223> OTHER INFORMATION: Primer RS6803-5

<400> SEQUENCE: 8
attgctgaag cggaatccct g    21

<210> SEQ ID NO 9
<211> LENGTH: 58
<212> TYPE: DNA
<213> ORGANISM: Artificial Sequence
<220> FEATURE:
<223> OTHER INFORMATION: Primer RSMCS-3

<400> SEQUENCE: 9
catggagatc tgagctcgca tgcatatggt accatataac catcaaagcc atagttgg    58

<210> SEQ ID NO 10
<211> LENGTH: 58
<212> TYPE: DNA
<213> ORGANISM: Artificial Sequence
<220> FEATURE:
<223> OTHER INFORMATION: Primer RSMCS-5

<400> SEQUENCE: 10
atatgcatgc gagctcagat ctccatggaa ttcggtaccg gtatggatgg caccgatg    58

<210> SEQ ID NO 11
<211> LENGTH: 21
<212> TYPE: DNA
<213> ORGANISM: Artificial Sequence
<220> FEATURE:
<223> OTHER INFORMATION: Primer RS6803-3

<400> SEQUENCE: 11
tgggggacca ttctctggat c    21

<210> SEQ ID NO 12
<211> LENGTH: 39
<212> TYPE: DNA
<213> ORGANISM: Artificial Sequence
<220> FEATURE:
<223> OTHER INFORMATION: Primer NS2-5MCS

<400> SEQUENCE: 12
gcatgcgagc tcagatctac caggttgtcc ttggcgcag    39

<210> SEQ ID NO 13
<211> LENGTH: 39
<212> TYPE: DNA
<213> ORGANISM: Artificial Sequence
<220> FEATURE:
<223> OTHER INFORMATION: Primer NS21-3MCS

<400> SEQUENCE: 13
ccataccggt accgaattcg ccacgttact gctcgatgg    39

<210> SEQ ID NO 14
<211> LENGTH: 90
<212> TYPE: DNA
<213> ORGANISM: Artificial Sequence

```
<220> FEATURE:
<223> OTHER INFORMATION: TrcY promoter

<400> SEQUENCE: 14
ctgaaatgag ctgttgacaa ttaatcatcc ggctcgtata atgtgtggaa ttgtgagcgg     60
ataacaattt cacactaagg aggaaaaaaa                                     90

<210> SEQ ID NO 15
<211> LENGTH: 70
<212> TYPE: DNA
<213> ORGANISM: Artificial Sequence
<220> FEATURE:
<223> OTHER INFORMATION: Primer 4YC-trc-Y-5

<400> SEQUENCE: 15
actagtcctg aggctgaaat gagctgttga caattaatca tccggctcgt ataatgtgtg     60
gaattgtgag                                                           70

<210> SEQ ID NO 16
<211> LENGTH: 69
<212> TYPE: DNA
<213> ORGANISM: Artificial Sequence
<220> FEATURE:
<223> OTHER INFORMATION: Primer 4YC-trcY-3

<400> SEQUENCE: 16
ccatggtttt tttcctcctt actctcaaat tgttatccgc tcacaattcc acacattata     60
cgaccggat                                                            69

<210> SEQ ID NO 17
<211> LENGTH: 31
<212> TYPE: DNA
<213> ORGANISM: Artificial Sequence
<220> FEATURE:
<223> OTHER INFORMATION: Primer RS2-5

<400> SEQUENCE: 17
gggccctatt tgcccgtatt ctgccctatc c                                   31

<210> SEQ ID NO 18
<211> LENGTH: 32
<212> TYPE: DNA
<213> ORGANISM: Artificial Sequence
<220> FEATURE:
<223> OTHER INFORMATION: Primer RS2-3

<400> SEQUENCE: 18
gggcccgact gcctttggtg gtattaccga tg                                  32

<210> SEQ ID NO 19
<211> LENGTH: 52
<212> TYPE: DNA
<213> ORGANISM: Artificial Sequence
<220> FEATURE:
<223> OTHER INFORMATION: Primer YC-245

<400> SEQUENCE: 19
aaagcttagg cctgcagata tctagattaa ctggcgggat taccattact gg            52

<210> SEQ ID NO 20
<211> LENGTH: 25
<212> TYPE: DNA
<213> ORGANISM: Artificial Sequence
<220> FEATURE:
```

```
<223> OTHER INFORMATION: Primer NB001

<400> SEQUENCE: 20
ctcgagcccc cgtgctatga ctagc                                              25

<210> SEQ ID NO 21
<211> LENGTH: 26
<212> TYPE: DNA
<213> ORGANISM: Artificial Sequence
<220> FEATURE:
<223> OTHER INFORMATION: Primer NB002

<400> SEQUENCE: 21
ctcgagcgga acgtttttg taccccc                                             26

<210> SEQ ID NO 22
<211> LENGTH: 29
<212> TYPE: DNA
<213> ORGANISM: Artificial Sequence
<220> FEATURE:
<223> OTHER INFORMATION: Primer NB010

<400> SEQUENCE: 22
caattggtca cacgggataa taccgcgcc                                          29

<210> SEQ ID NO 23
<211> LENGTH: 37
<212> TYPE: DNA
<213> ORGANISM: Artificial Sequence
<220> FEATURE:
<223> OTHER INFORMATION: Primer NB011

<400> SEQUENCE: 23
caattggtcg catcatatcg tcaattatta cctccac                                 37

<210> SEQ ID NO 24
<211> LENGTH: 49
<212> TYPE: DNA
<213> ORGANISM: Artificial Sequence
<220> FEATURE:
<223> OTHER INFORMATION: Primer YC-253

<400> SEQUENCE: 24
gcttctcaaa tgcctgaggt atactgaaat gagctgttga caattaatc                    49

<210> SEQ ID NO 25
<211> LENGTH: 37
<212> TYPE: DNA
<213> ORGANISM: Artificial Sequence
<220> FEATURE:
<223> OTHER INFORMATION: Primer YC-254

<400> SEQUENCE: 25
tgagcaaact ggcctcagga tcgggcctgg cacccag                                 37
```